(12) United States Patent
Rothenberg

(10) Patent No.: US 8,512,256 B2
(45) Date of Patent: Aug. 20, 2013

(54) METHOD OF LOCATING THE TIP OF A CENTRAL VENOUS CATHETER

(75) Inventor: Peter M. Rothenberg, Laguna Niguel, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 36 days.

(21) Appl. No.: 12/878,915

(22) Filed: Sep. 9, 2010

(65) Prior Publication Data

US 2010/0331712 A1 Dec. 30, 2010

Related U.S. Application Data

(62) Division of application No. 11/552,094, filed on Oct. 23, 2006, now Pat. No. 7,794,407.

(51) Int. Cl.
*A61B 5/02* (2006.01)
*A61B 5/04* (2006.01)
*A61B 5/05* (2006.01)

(52) U.S. Cl.
USPC ............ 600/508; 600/509; 600/510; 600/424

(58) Field of Classification Search
USPC .................. 600/508, 509, 510, 424; 607/28, 607/122
See application file for complete search history.

(56) References Cited

U.S. PATENT DOCUMENTS

| | | | |
|---|---|---|---|
| 3,133,244 A | 5/1964 | Wojtulewicz | |
| 3,297,020 A | 1/1967 | Mathiesen | |
| 3,625,200 A | 12/1971 | Muller | |
| 3,674,014 A | 7/1972 | Tillander et al. | |
| 3,817,241 A | 6/1974 | Grausz | |
| 3,847,157 A | 11/1974 | Caillouette et al. | |
| 3,868,565 A | 2/1975 | Kuipers | |
| 3,902,501 A | 9/1975 | Citron et al. | |
| 3,995,623 A | 12/1976 | Blake et al. | |

(Continued)

FOREIGN PATENT DOCUMENTS

| | | |
|---|---|---|
| AU | 642647 | 11/1990 |
| AU | 1860597 B2 | 6/1999 |

(Continued)

OTHER PUBLICATIONS

CN 200880012117.4 filed Apr. 16, 2008 First Office Action dated Dec. 23, 2011.

(Continued)

*Primary Examiner* — Niketa Patel
*Assistant Examiner* — William Levicky
(74) *Attorney, Agent, or Firm* — Rutan & Tucker, LLP

(57) ABSTRACT

A method of locating a tip of a central venous catheter ("CVC") having a distal and proximal pair of electrodes disposed within the superior vena cava, right atrium, and/or right ventricle. The method includes obtaining a distal and proximal electrical signal from the distal and proximal pair of electrodes and using those signals to generate a distal and proximal P wave, respectively. A deflection value is determined for each of the P waves. A ratio of the deflection values is then used to determine a location of the tip of the CVC. Optionally, the CVC may include a reference pair of electrodes disposed within the superior vena cava from which a reference deflection value may be obtained. A ratio of one of the other deflection values to the reference deflection value may be used to determine the location of the tip of the CVC.

11 Claims, 7 Drawing Sheets

(56) References Cited

U.S. PATENT DOCUMENTS

| | | |
|---|---|---|
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder et al. |
| 4,173,228 A | 11/1979 | Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A * | 3/1986 | Gessman .................. 607/14 |
| 4,582,067 A | 4/1986 | Silverstein et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner et al. |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,622 A | 6/1989 | Hardy |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,995,396 A | 2/1991 | Inaba et al. |
| 4,998,916 A | 3/1991 | Hammerslag et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A * | 1/1992 | Katims .................. 604/28 |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A * | 6/1992 | Katims .................. 600/547 |
| 5,134,370 A | 7/1992 | Jefferts et al. |
| 5,144,955 A | 9/1992 | O'Hara |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,184,601 A | 2/1993 | Putman |
| 5,190,045 A | 3/1993 | Frazin |
| 5,202,985 A | 4/1993 | Goyal |
| 5,211,165 A | 5/1993 | Dumoulin et al. |
| 5,211,636 A | 5/1993 | Mische |
| 5,214,615 A | 5/1993 | Bauer et al. |
| 5,217,026 A | 6/1993 | Stoy et al. |
| 5,220,924 A | 6/1993 | Frazin |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |

| Patent | Date | Inventor |
|---|---|---|
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout et al. |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,422,478 A | 6/1995 | Wlodarczyk et al. |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada et al. |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,450,846 A | 9/1995 | Goldreyer |
| 5,453,575 A | 9/1995 | O'Donnell et al. |
| 5,456,256 A | 10/1995 | Schneider |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,853 A | 5/1996 | Smith et al. |
| 5,522,878 A | 6/1996 | Montecalvo et al. |
| 5,526,812 A | 6/1996 | Dumoulin et al. |
| 5,531,664 A | 7/1996 | Adachi et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,558,091 A | 9/1996 | Acker et al. |
| 5,568,809 A | 10/1996 | Ben-haim |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| 5,662,115 A | 9/1997 | Torp et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,713,362 A | 2/1998 | Vilkomerson |
| 5,713,363 A | 2/1998 | Seward et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman et al. |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,779,638 A | 7/1998 | Vesely et al. |
| 5,782,767 A | 7/1998 | Pretlow, III |
| 5,785,657 A | 7/1998 | Breyer et al. |
| 5,792,055 A | 8/1998 | McKinnon et al. |
| 5,795,297 A | 8/1998 | Daigle |
| 5,795,298 A | 8/1998 | Vesely et al. |

| Patent | Date | Inventor |
|---|---|---|
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,107,699 A | 8/2000 | Swanson |
| 6,112,111 A | 8/2000 | Glantz |
| 6,113,504 A | 9/2000 | Kuesters |
| 6,115,624 A | 9/2000 | Lewis et al. |
| 6,120,445 A | 9/2000 | Grunwald |
| 6,128,174 A | 10/2000 | Ritter et al. |
| 6,129,668 A | 10/2000 | Haynor et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,144,300 A | 11/2000 | Dames et al. |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,193,743 B1 | 2/2001 | Brayton et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |
| 6,223,087 B1 | 4/2001 | Williams |
| 6,226,547 B1 | 5/2001 | Lockhart et al. |
| 6,230,046 B1 | 5/2001 | Crane et al. |
| 6,233,476 B1 | 5/2001 | Strommer et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,253,770 B1 | 7/2001 | Acker et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,271,833 B1 | 8/2001 | Rosenberg et al. |
| 6,272,371 B1 | 8/2001 | Shlomo |
| 6,272,374 B1 | 8/2001 | Flock et al. |

| | | |
|---|---|---|
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames et al. |
| 6,323,770 B1 | 11/2001 | Dames et al. |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames et al. |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,355,026 B1 | 3/2002 | Mick |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames et al. |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,401,723 B1 | 6/2002 | Garibaldi et al. |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,459,919 B1 | 10/2002 | Lys et al. |
| 6,463,121 B1 | 10/2002 | Milnes |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari et al. |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,507,751 B2 | 1/2003 | Blume et al. |
| 6,508,802 B1 | 1/2003 | Rosengart et al. |
| 6,512,958 B1 | 1/2003 | Swoyer et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith et al. |
| 6,542,766 B2 | 4/2003 | Hall et al. |
| 6,544,251 B1 | 4/2003 | Crawford |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,506 B2 | 11/2003 | Bowe et al. |
| 6,662,034 B2 | 12/2003 | Segner et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |

| Patent | Kind | Date | Inventor |
|---|---|---|---|
| 6,701,918 | B2 | 3/2004 | Fariss et al. |
| 6,702,804 | B1 | 3/2004 | Ritter et al. |
| 6,704,590 | B2 | 3/2004 | Haldeman |
| 6,709,390 | B1 | 3/2004 | Marie Pop |
| 6,711,429 | B1 | 3/2004 | Gilboa et al. |
| 6,711,431 | B2 | 3/2004 | Sarin et al. |
| 6,719,699 | B2 | 4/2004 | Smith |
| 6,719,724 | B1 | 4/2004 | Walker et al. |
| 6,719,756 | B1 | 4/2004 | Muntermann |
| 6,720,745 | B2 | 4/2004 | Lys et al. |
| 6,733,511 | B2 | 5/2004 | Hall et al. |
| 6,736,782 | B2 | 5/2004 | Pfeiffer et al. |
| 6,738,656 | B1 | 5/2004 | Ferre et al. |
| 6,740,103 | B2 | 5/2004 | Hall et al. |
| 6,743,177 | B2 | 6/2004 | Ito et al. |
| 6,754,596 | B2 | 6/2004 | Ashe |
| 6,755,789 | B2 | 6/2004 | Stringer et al. |
| 6,755,816 | B2 | 6/2004 | Ritter et al. |
| 6,757,557 | B1 | 6/2004 | Bladen et al. |
| 6,763,261 | B2 | 7/2004 | Casscells, III et al. |
| 6,764,449 | B2 | 7/2004 | Lee et al. |
| 6,768,496 | B2 | 7/2004 | Bieger et al. |
| 6,772,001 | B2 | 8/2004 | Maschke et al. |
| 6,774,624 | B2 | 8/2004 | Anderson et al. |
| 6,783,536 | B2 | 8/2004 | Vilsmeier et al. |
| 6,784,660 | B2 | 8/2004 | Ashe |
| 6,785,571 | B2 | 8/2004 | Glossop |
| 6,786,219 | B2 | 9/2004 | Garibaldi et al. |
| 6,788,967 | B2 | 9/2004 | Ben-Haim et al. |
| 6,794,667 | B2 | 9/2004 | Noshi |
| 6,799,066 | B2 | 9/2004 | Steines et al. |
| 6,815,651 | B2 | 11/2004 | Odell |
| 6,816,266 | B2 | 11/2004 | Varshneya et al. |
| 6,817,364 | B2 | 11/2004 | Garibaldi |
| 6,834,201 | B2 | 12/2004 | Gillies et al. |
| 6,844,713 | B2 | 1/2005 | Steber et al. |
| 6,845,142 | B2 | 1/2005 | Ohishi |
| 6,856,823 | B2 | 2/2005 | Ashe |
| 6,860,422 | B2 | 3/2005 | Hull et al. |
| 6,862,467 | B2 | 3/2005 | Moore et al. |
| 6,869,390 | B2 | 3/2005 | Elliott et al. |
| 6,875,179 | B2 | 4/2005 | Ferguson et al. |
| 6,879,160 | B2 | 4/2005 | Jakab |
| 6,889,091 | B2 | 5/2005 | Hine et al. |
| 6,895,268 | B1 | 5/2005 | Rahn et al. |
| 6,902,528 | B1 | 6/2005 | Garibaldi et al. |
| 6,908,433 | B1 | 6/2005 | Pruter |
| 6,911,026 | B1 | 6/2005 | Hall et al. |
| 6,923,782 | B2 | 8/2005 | O'Mahony et al. |
| 6,926,673 | B2 | 8/2005 | Roberts et al. |
| 6,934,575 | B2 | 8/2005 | Ferre et al. |
| 6,936,010 | B2 | 8/2005 | Fang et al. |
| 6,940,379 | B2 | 9/2005 | Creighton |
| 6,941,166 | B2 | 9/2005 | MacAdam et al. |
| 6,947,788 | B2 | 9/2005 | Gilboa et al. |
| 6,950,689 | B1 | 9/2005 | Willis et al. |
| 6,953,754 | B2 | 10/2005 | Machida et al. |
| 6,958,677 | B1 | 10/2005 | Carter |
| 6,959,214 | B2 | 10/2005 | Pape et al. |
| 6,962,566 | B2 | 11/2005 | Quistgaard et al. |
| 6,968,846 | B2 | 11/2005 | Viswanathan |
| 6,975,197 | B2 | 12/2005 | Creighton, IV |
| 6,976,962 | B2 | 12/2005 | Bullis |
| 6,976,987 | B2 | 12/2005 | Flores |
| 6,980,843 | B2 | 12/2005 | Eng et al. |
| 6,980,852 | B2 | 12/2005 | Jersey-Willuhn et al. |
| 6,980,921 | B2 | 12/2005 | Anderson et al. |
| 6,986,739 | B2 | 1/2006 | Warren et al. |
| 6,999,821 | B2 | 2/2006 | Jenney et al. |
| 7,001,355 | B2 | 2/2006 | Nunomura et al. |
| 7,008,418 | B2 | 3/2006 | Hall et al. |
| 7,010,338 | B2 | 3/2006 | Ritter et al. |
| 7,015,393 | B2 | 3/2006 | Weiner et al. |
| 7,017,584 | B2 | 3/2006 | Garibaldi et al. |
| 7,019,610 | B2 | 3/2006 | Creighton, IV et al. |
| 7,020,512 | B2 | 3/2006 | Ritter et al. |
| 7,022,075 | B2 | 4/2006 | Grunwald et al. |
| 7,022,082 | B2 | 4/2006 | Sonek |
| 7,026,927 | B2 | 4/2006 | Wright et al. |
| 7,027,634 | B2 | 4/2006 | Odell |
| 7,028,387 | B1 | 4/2006 | Huynh et al. |
| 7,029,446 | B2 | 4/2006 | Wendelken et al. |
| 7,033,603 | B2 | 4/2006 | Nelson et al. |
| 7,038,398 | B1 | 5/2006 | Lys et al. |
| 7,038,657 | B2 | 5/2006 | Rosenberg et al. |
| 7,043,293 | B1 | 5/2006 | Baura |
| 7,054,228 | B1 | 5/2006 | Hickling |
| 7,066,914 | B2 | 6/2006 | Andersen |
| 7,066,924 | B1 | 6/2006 | Garibaldi et al. |
| 7,070,565 | B2 | 7/2006 | Vaezy et al. |
| 7,072,704 | B2 | 7/2006 | Bucholz |
| 7,082,325 | B2 | 7/2006 | Hashimshony et al. |
| 7,090,639 | B2 | 8/2006 | Govari |
| 7,096,148 | B2 | 8/2006 | Anderson et al. |
| 7,096,870 | B2 | 8/2006 | Lamprich et al. |
| 7,098,907 | B2 | 8/2006 | Houston et al. |
| 7,103,205 | B2 | 9/2006 | Wang et al. |
| 7,104,980 | B1 | 9/2006 | Laherty et al. |
| 7,106,043 | B1 | 9/2006 | Da Silva et al. |
| 7,106,431 | B2 | 9/2006 | Odell |
| 7,106,479 | B2 | 9/2006 | Roy et al. |
| 7,107,105 | B2 | 9/2006 | Bjorklund et al. |
| 7,132,804 | B2 | 11/2006 | Lys et al. |
| 7,137,976 | B2 | 11/2006 | Ritter et al. |
| 7,141,812 | B2 | 11/2006 | Appleby et al. |
| 7,142,905 | B2 | 11/2006 | Slayton et al. |
| 7,148,970 | B2 | 12/2006 | de Boer |
| 7,153,291 | B2 | 12/2006 | Bierman |
| 7,161,453 | B2 | 1/2007 | Creighton, IV |
| 7,162,291 | B1 | 1/2007 | Nachaliel |
| 7,167,738 | B2 | 1/2007 | Schweikard et al. |
| 7,169,107 | B2 | 1/2007 | Jersey-Willuhn et al. |
| 7,174,201 | B2 | 2/2007 | Govari et al. |
| 7,175,646 | B2 | 2/2007 | Brenneman et al. |
| 7,180,252 | B2 | 2/2007 | Lys et al. |
| 7,184,820 | B2 | 2/2007 | Jersey-Willuhn et al. |
| 7,189,198 | B2 | 3/2007 | Harburn et al. |
| 7,190,819 | B2 | 3/2007 | Viswanathan |
| 7,194,295 | B2 | 3/2007 | Vilsmeier |
| 7,204,798 | B2 | 4/2007 | Zdeblick et al. |
| 7,206,064 | B2 | 4/2007 | Rogers et al. |
| 7,207,941 | B2 | 4/2007 | Sharf |
| 7,211,082 | B2 | 5/2007 | Hall et al. |
| 7,214,191 | B2 | 5/2007 | Stringer et al. |
| 7,215,326 | B2 | 5/2007 | Rosenberg |
| 7,221,104 | B2 | 5/2007 | Lys et al. |
| 7,223,256 | B2 | 5/2007 | Bierman |
| 7,229,400 | B2 | 6/2007 | Elliott et al. |
| 7,231,243 | B2 | 6/2007 | Tearney et al. |
| 7,236,157 | B2 | 6/2007 | Schena et al. |
| 7,236,816 | B2 | 6/2007 | Kumar et al. |
| 7,237,313 | B2 | 7/2007 | Skujins et al. |
| 7,241,267 | B2 | 7/2007 | Furia |
| 7,244,234 | B2 | 7/2007 | Ridley et al. |
| 7,248,032 | B1 | 7/2007 | Hular et al. |
| 7,248,914 | B2 | 7/2007 | Hastings et al. |
| 7,264,584 | B2 | 9/2007 | Ritter et al. |
| 7,270,662 | B2 | 9/2007 | Visram et al. |
| 7,276,044 | B2 | 10/2007 | Ferry et al. |
| 7,286,034 | B2 | 10/2007 | Creighton |
| 7,291,146 | B2 | 11/2007 | Steinke et al. |
| 7,297,140 | B2 | 11/2007 | Orlu et al. |
| 7,308,296 | B2 | 12/2007 | Lys et al. |
| 7,310,150 | B2 | 12/2007 | Guillermo et al. |
| 7,321,228 | B2 | 1/2008 | Govari |
| 7,342,058 | B2 | 3/2008 | Peppmoller et al. |
| 7,355,716 | B2 | 4/2008 | de Boer et al. |
| 7,360,427 | B2 | 4/2008 | Drinkwater et al. |
| 7,366,376 | B2 | 4/2008 | Shishkov et al. |
| 7,366,562 | B2 | 4/2008 | Dukesherer et al. |
| 7,366,563 | B2 | 4/2008 | Kleen et al. |
| 7,373,271 | B1 | 5/2008 | Schneider |
| 7,382,949 | B2 | 6/2008 | Bouma et al. |
| 7,418,169 | B2 | 8/2008 | Tearney et al. |
| 7,447,408 | B2 | 11/2008 | Bouma et al. |
| 7,452,358 | B2 | 11/2008 | Stern et al. |
| 7,479,141 | B2 | 1/2009 | Kleen et al. |
| 7,534,223 | B2 | 5/2009 | Boutilette et al. |

| | | | | | | |
|---|---|---|---|---|---|---|
| 7,538,859 B2 | 5/2009 | Tearney et al. | | 2004/0097803 A1 | 5/2004 | Panescu |
| 7,547,282 B2 | 6/2009 | Lo et al. | | 2004/0097804 A1 | 5/2004 | Sobe |
| 7,551,293 B2 | 6/2009 | Yelin et al. | | 2004/0097805 A1 | 5/2004 | Verard et al. |
| 7,599,730 B2 | 10/2009 | Hunter et al. | | 2004/0097806 A1 | 5/2004 | Hunter et al. |
| 7,635,336 B1 | 12/2009 | Pruter | | 2004/0116809 A1 | 6/2004 | Chow et al. |
| 7,637,163 B2 | 12/2009 | Fetzer et al. | | 2004/0127805 A1 | 7/2004 | MacAdam et al. |
| 7,640,053 B2 | 12/2009 | Verin | | 2004/0131998 A1 | 7/2004 | Marom et al. |
| 7,651,469 B2 | 1/2010 | Osborne et al. | | 2004/0133111 A1 | 7/2004 | Szczech et al. |
| 7,652,080 B2 | 1/2010 | Peppmoller et al. | | 2004/0133130 A1 | 7/2004 | Ferry et al. |
| 7,665,893 B2 | 2/2010 | Buchalter | | 2004/0135069 A1 | 7/2004 | Odell |
| 7,668,583 B2 | 2/2010 | Fegert et al. | | 2004/0138564 A1 | 7/2004 | Hwang et al. |
| 7,699,782 B2 | 4/2010 | Angelsen et al. | | 2004/0138570 A1 | 7/2004 | Nita et al. |
| 7,727,192 B2 | 6/2010 | Tokumoto et al. | | 2004/0147837 A1 | 7/2004 | Macaulay et al. |
| 7,751,865 B2 | 7/2010 | Jascob et al. | | 2004/0150963 A1 | 8/2004 | Holmberg et al. |
| 7,766,839 B2 | 8/2010 | Rogers et al. | | 2004/0152972 A1 | 8/2004 | Hunter |
| 7,774,051 B2 | 8/2010 | Voth | | 2004/0155609 A1 | 8/2004 | Lys et al. |
| 7,794,407 B2 | 9/2010 | Rothenberg | | 2004/0158140 A1 | 8/2004 | Fuimaono et al. |
| 7,798,970 B2 | 9/2010 | Lo et al. | | 2004/0171924 A1 | 9/2004 | Mire et al. |
| 7,819,810 B2 | 10/2010 | Stringer et al. | | 2004/0176688 A1 | 9/2004 | Haldeman |
| 7,850,613 B2 | 12/2010 | Stribling | | 2004/0186461 A1 | 9/2004 | DiMatteo |
| 7,909,815 B2 | 3/2011 | Whitmore, III et al. | | 2004/0199069 A1 | 10/2004 | Connelly et al. |
| 7,931,596 B2 | 4/2011 | Rachlin et al. | | 2004/0210289 A1 | 10/2004 | Wang et al. |
| 7,976,469 B2 | 7/2011 | Bonde et al. | | 2004/0230271 A1 | 11/2004 | Wang et al. |
| 8,118,743 B2 | 2/2012 | Park et al. | | 2004/0234453 A1 | 11/2004 | Smith |
| 8,388,541 B2 | 3/2013 | Messerly et al. | | 2004/0253365 A1 | 12/2004 | Warren et al. |
| 8,388,546 B2 | 3/2013 | Rothenberg | | 2004/0254470 A1 | 12/2004 | Drinkwater et al. |
| 2002/0019447 A1 | 2/2002 | Renn et al. | | 2004/0260174 A1 | 12/2004 | Keene |
| 2002/0022777 A1 | 2/2002 | Crieghton et al. | | 2004/0267086 A1 | 12/2004 | Anstadt et al. |
| 2002/0032391 A1 | 3/2002 | McFann et al. | | 2005/0004450 A1 | 1/2005 | Ben-Haim et al. |
| 2002/0055680 A1 | 5/2002 | Miele et al. | | 2005/0021019 A1 | 1/2005 | Hashimshony et al. |
| 2002/0082559 A1 | 6/2002 | Chang et al. | | 2005/0033150 A1 | 2/2005 | Takahashi et al. |
| 2002/0113555 A1 | 8/2002 | Lys et al. | | 2005/0038355 A1 | 2/2005 | Gellman et al. |
| 2002/0123679 A1 | 9/2002 | Dominguez | | 2005/0049486 A1 | 3/2005 | Urquhart et al. |
| 2002/0128554 A1 | 9/2002 | Seward | | 2005/0049510 A1 | 3/2005 | Haldeman et al. |
| 2002/0133079 A1 | 9/2002 | Sandhu | | 2005/0063194 A1 | 3/2005 | Lys et al. |
| 2002/0156363 A1 | 10/2002 | Hunter et al. | | 2005/0070788 A1 | 3/2005 | Wilson et al. |
| 2002/0156376 A1 | 10/2002 | Wang et al. | | 2005/0075561 A1 | 4/2005 | Golden |
| 2002/0165448 A1 | 11/2002 | Ben-Haim et al. | | 2005/0085716 A1 | 4/2005 | Hamm et al. |
| 2002/0165534 A1 | 11/2002 | Hayzelden et al. | | 2005/0085718 A1 | 4/2005 | Shahidi |
| 2002/0198568 A1 | 12/2002 | Hafer et al. | | 2005/0085720 A1 | 4/2005 | Jascob et al. |
| 2003/0009132 A1 | 1/2003 | Schwartz et al. | | 2005/0101868 A1 | 5/2005 | Ridley et al. |
| 2003/0011359 A1 | 1/2003 | Ashe | | 2005/0101869 A1 | 5/2005 | Burba et al. |
| 2003/0013966 A1 | 1/2003 | Barnes et al. | | 2005/0105081 A1 | 5/2005 | Odell |
| 2003/0036696 A1 | 2/2003 | Willis et al. | | 2005/0105101 A1 | 5/2005 | Duling et al. |
| 2003/0040671 A1 | 2/2003 | Somogyi et al. | | 2005/0112135 A1 | 5/2005 | Cormier et al. |
| 2003/0072805 A1 | 4/2003 | Miyazawa et al. | | 2005/0113669 A1 | 5/2005 | Helfer et al. |
| 2003/0076281 A1 | 4/2003 | Morgan et al. | | 2005/0113676 A1 | 5/2005 | Weiner et al. |
| 2003/0083698 A1 | 5/2003 | Whitehurst et al. | | 2005/0113700 A1 | 5/2005 | Yanagihara et al. |
| 2003/0088195 A1 | 5/2003 | Vardi et al. | | 2005/0113873 A1 | 5/2005 | Weiner et al. |
| 2003/0100849 A1 | 5/2003 | Jang | | 2005/0113874 A1 | 5/2005 | Connelly et al. |
| 2003/0114742 A1 | 6/2003 | Lewkowicz et al. | | 2005/0113876 A1 | 5/2005 | Weiner et al. |
| 2003/0114777 A1 | 6/2003 | Griffin et al. | | 2005/0149002 A1 | 7/2005 | Wang et al. |
| 2003/0120150 A1 | 6/2003 | Govari | | 2005/0151489 A1 | 7/2005 | Lys et al. |
| 2003/0120154 A1 | 6/2003 | Sauer et al. | | 2005/0154308 A1 | 7/2005 | Quistgaard et al. |
| 2003/0139661 A1 | 7/2003 | Kimchy et al. | | 2005/0159644 A1 | 7/2005 | Takano |
| 2003/0149328 A1 | 8/2003 | Elliott et al. | | 2005/0159790 A1 | 7/2005 | Shalev |
| 2003/0152290 A1 | 8/2003 | Odell | | 2005/0165301 A1 | 7/2005 | Smith et al. |
| 2003/0160721 A1 | 8/2003 | Gilboa et al. | | 2005/0165313 A1 | 7/2005 | Byron et al. |
| 2003/0163037 A1 | 8/2003 | Bladen et al. | | 2005/0175665 A1 | 8/2005 | Hunter et al. |
| 2003/0171691 A1 | 9/2003 | Casscells et al. | | 2005/0175703 A1 | 8/2005 | Hunter et al. |
| 2003/0173953 A1 | 9/2003 | Ashe | | 2005/0178395 A1 | 8/2005 | Hunter et al. |
| 2003/0184544 A1 | 10/2003 | Prudent | | 2005/0178396 A1 | 8/2005 | Hunter et al. |
| 2003/0191392 A1 | 10/2003 | Haldeman | | 2005/0182295 A1 | 8/2005 | Soper et al. |
| 2003/0191460 A1 | 10/2003 | Hobbs et al. | | 2005/0203368 A1 | 9/2005 | Verin |
| 2003/0195420 A1 | 10/2003 | Mendlein et al. | | 2005/0203396 A1 | 9/2005 | Angelsen et al. |
| 2003/0199746 A1 | 10/2003 | Fuimaono et al. | | 2005/0205081 A1 | 9/2005 | Barker et al. |
| 2003/0208142 A1 | 11/2003 | Boudewijn et al. | | 2005/0215901 A1 | 9/2005 | Anderson et al. |
| 2003/0216639 A1 | 11/2003 | Gilboa et al. | | 2005/0215945 A1 | 9/2005 | Harris et al. |
| 2003/0220557 A1 | 11/2003 | Cleary et al. | | 2005/0222532 A1 | 10/2005 | Bertolero et al. |
| 2003/0220578 A1 | 11/2003 | Ho et al. | | 2005/0240102 A1 | 10/2005 | Rachlin et al. |
| 2003/0229298 A1 | 12/2003 | Iwami et al. | | 2005/0256398 A1 | 11/2005 | Hastings et al. |
| 2003/0233042 A1 | 12/2003 | Ashe | | 2005/0256541 A1 | 11/2005 | Stypulkowski |
| 2004/0015070 A1 | 1/2004 | Liang et al. | | 2006/0015003 A1 | 1/2006 | Moaddes et al. |
| 2004/0024301 A1 | 2/2004 | Hockett et al. | | 2006/0025677 A1 | 2/2006 | Verard et al. |
| 2004/0030319 A1 | 2/2004 | Korkor et al. | | 2006/0058633 A1 | 3/2006 | Hoshino et al. |
| 2004/0054278 A1 | 3/2004 | Kimchy et al. | | 2006/0068074 A1 | 3/2006 | Stefandl |
| 2004/0082916 A1 | 4/2004 | Jenkins | | 2006/0084867 A1 | 4/2006 | Tremblay et al. |
| 2004/0087877 A1 | 5/2004 | Besz et al. | | 2006/0116571 A1 | 6/2006 | Maschke et al. |
| 2004/0088136 A1 | 5/2004 | Ashe | | 2006/0116578 A1 | 6/2006 | Grunwald et al. |

| | | | | | | |
|---|---|---|---|---|---|---|
| 2006/0149134 A1 | 7/2006 | Soper et al. | | 2009/0043205 A1 | 2/2009 | Pelissier et al. |
| 2006/0173329 A1 | 8/2006 | Irioka et al. | | 2009/0082661 A1 | 3/2009 | Saladin et al. |
| 2006/0173407 A1 | 8/2006 | Shaughnessy et al. | | 2009/0084382 A1 | 4/2009 | Jalde et al. |
| 2006/0176242 A1 | 8/2006 | Jaramaz et al. | | 2009/0101577 A1 | 4/2009 | Fulkerson et al. |
| 2006/0184074 A1 | 8/2006 | Vaezy et al. | | 2009/0118612 A1 | 5/2009 | Grunwald et al. |
| 2006/0206037 A1 | 9/2006 | Braxton | | 2009/0118706 A1 | 5/2009 | Schweikert et al. |
| 2006/0211944 A1 | 9/2006 | Mauge et al. | | 2009/0143736 A1 | 6/2009 | Mittermeyer et al. |
| 2006/0224188 A1 | 10/2006 | Libbus et al. | | 2009/0156926 A1 | 6/2009 | Messerly et al. |
| 2006/0247746 A1 | 11/2006 | Danek et al. | | 2009/0163810 A1 | 6/2009 | Kanade et al. |
| 2006/0276867 A1 | 12/2006 | Viswanathan | | 2009/0171217 A1 | 7/2009 | Kim et al. |
| 2007/0010753 A1 | 1/2007 | MacAdam | | 2009/0177083 A1 | 7/2009 | Matsumura |
| 2007/0016007 A1 | 1/2007 | Govari et al. | | 2009/0177090 A1 | 7/2009 | Grunwald et al. |
| 2007/0016013 A1 | 1/2007 | Camus | | 2009/0203989 A1 | 8/2009 | Burnside et al. |
| 2007/0016068 A1 | 1/2007 | Grunwald et al. | | 2009/0204113 A1 | 8/2009 | MacAdam et al. |
| 2007/0016069 A1 | 1/2007 | Grunwald et al. | | 2009/0209950 A1 | 8/2009 | Starksen |
| 2007/0016070 A1 | 1/2007 | Grunwald et al. | | 2009/0227952 A1 | 9/2009 | Blakstvedt et al. |
| 2007/0016072 A1 | 1/2007 | Grunwald et al. | | 2009/0234328 A1 | 9/2009 | Cox et al. |
| 2007/0049822 A1 | 3/2007 | Bunce et al. | | 2009/0258171 A1 | 10/2009 | Uang |
| 2007/0049846 A1 | 3/2007 | Bown et al. | | 2009/0259124 A1 | 10/2009 | Rothenberg |
| 2007/0055141 A1 | 3/2007 | Kruger et al. | | 2009/0262982 A1 | 10/2009 | Markowitz et al. |
| 2007/0055142 A1 | 3/2007 | Webler | | 2009/0275828 A1 | 11/2009 | Shachar et al. |
| 2007/0060992 A1 | 3/2007 | Pappone | | 2009/0297441 A1 | 12/2009 | Canham et al. |
| 2007/0062544 A1 | 3/2007 | Bergstrom et al. | | 2010/0004543 A1 | 1/2010 | Ahlund et al. |
| 2007/0073155 A1 | 3/2007 | Park et al. | | 2010/0004547 A1 | 1/2010 | Scholz et al. |
| 2007/0087038 A1 | 4/2007 | Richardson et al. | | 2010/0016726 A1 | 1/2010 | Meier |
| 2007/0093710 A1 | 4/2007 | Maschke | | 2010/0036227 A1 | 2/2010 | Cox et al. |
| 2007/0100285 A1 | 5/2007 | Griffin et al. | | 2010/0049062 A1 | 2/2010 | Ziv |
| 2007/0112282 A1 | 5/2007 | Skujins et al. | | 2010/0055153 A1 | 3/2010 | Majmudar |
| 2007/0123805 A1 | 5/2007 | Shireman et al. | | 2010/0055184 A1 | 3/2010 | Zeitels et al. |
| 2007/0129770 A1 | 6/2007 | Younis | | 2010/0057157 A1 | 3/2010 | Govari et al. |
| 2007/0135803 A1 | 6/2007 | Belson | | 2010/0060472 A1 | 3/2010 | Kimura et al. |
| 2007/0135886 A1 | 6/2007 | Maschke | | 2010/0083719 A1 | 4/2010 | Peppmoller et al. |
| 2007/0156205 A1 | 7/2007 | Larson et al. | | 2010/0094116 A1 | 4/2010 | Silverstein |
| 2007/0161915 A1 | 7/2007 | Desai | | 2010/0106011 A1 | 4/2010 | Byrd et al. |
| 2007/0167738 A1 | 7/2007 | Timinger et al. | | 2010/0114573 A1 | 5/2010 | Huang et al. |
| 2007/0167801 A1 | 7/2007 | Webler et al. | | 2010/0143119 A1 | 6/2010 | Kooijman et al. |
| 2007/0167997 A1 | 7/2007 | Forsberg et al. | | 2010/0185097 A1 | 7/2010 | Hall |
| 2007/0197905 A1 | 8/2007 | Timinger et al. | | 2010/0198048 A1 | 8/2010 | Togawa |
| 2007/0208255 A1 | 9/2007 | Ridley et al. | | 2010/0204569 A1 | 8/2010 | Burnside et al. |
| 2007/0225589 A1 | 9/2007 | Viswanathan | | 2010/0217116 A1 | 8/2010 | Eck et al. |
| 2007/0225610 A1 | 9/2007 | Mickley et al. | | 2010/0222664 A1 | 9/2010 | Lemon et al. |
| 2007/0232882 A1 | 10/2007 | Glossop et al. | | 2010/0234733 A1 | 9/2010 | Wahlheim |
| 2007/0238984 A1 | 10/2007 | Maschke et al. | | 2010/0249598 A1 | 9/2010 | Smith et al. |
| 2007/0239018 A1 | 10/2007 | Fetzer et al. | | 2010/0258033 A1 | 10/2010 | Yang et al. |
| 2007/0244413 A1 | 10/2007 | Biggins | | 2010/0273895 A1 | 10/2010 | Stinchcomb et al. |
| 2007/0247454 A1 | 10/2007 | Rahn et al. | | 2010/0298702 A1 | 11/2010 | Rogers et al. |
| 2007/0249911 A1 | 10/2007 | Simon | | 2010/0317981 A1 | 12/2010 | Grunwald |
| 2007/0265526 A1 | 11/2007 | Govari et al. | | 2010/0318026 A1 | 12/2010 | Grunwald |
| 2007/0280974 A1 | 12/2007 | Son et al. | | 2011/0015527 A1 | 1/2011 | Heasty et al. |
| 2007/0282196 A1 | 12/2007 | Birk et al. | | 2011/0015533 A1 | 1/2011 | Cox et al. |
| 2007/0282197 A1 | 12/2007 | Bill et al. | | 2011/0040212 A1 | 2/2011 | Dietz et al. |
| 2007/0299352 A1 | 12/2007 | Harlev et al. | | 2011/0052694 A1 | 3/2011 | Stinchcomb et al. |
| 2008/0008745 A1 | 1/2008 | Stinchcomb et al. | | 2011/0087107 A1 | 4/2011 | Lindekugel et al. |
| 2008/0009720 A1 | 1/2008 | Schefelker et al. | | 2011/0196248 A1 | 8/2011 | Grunwald |
| 2008/0015442 A1 | 1/2008 | Watson et al. | | 2011/0282188 A1 | 11/2011 | Burnside et al. |
| 2008/0027320 A1 | 1/2008 | Bolorforosh et al. | | 2011/0295108 A1 | 12/2011 | Cox et al. |
| 2008/0045908 A1 | 2/2008 | Gould et al. | | 2011/0313293 A1 | 12/2011 | Lindekugel et al. |
| 2008/0051626 A1 | 2/2008 | Sato et al. | | 2012/0046562 A1 | 2/2012 | Powers et al. |
| 2008/0081958 A1 | 4/2008 | Denison et al. | | 2012/0059270 A1 | 3/2012 | Grunwald |
| 2008/0082136 A1 | 4/2008 | Gaudiani | | 2012/0095319 A1 | 4/2012 | Kondrosky et al. |
| 2008/0097232 A1 | 4/2008 | Rothenberg | | 2012/0108950 A1 | 5/2012 | He et al. |
| 2008/0108949 A1 | 5/2008 | Beasley et al. | | 2012/0143029 A1 | 6/2012 | Silverstein et al. |
| 2008/0114095 A1 | 5/2008 | Peppmoller et al. | | 2012/0220854 A1 | 8/2012 | Messerly et al. |
| 2008/0125772 A1 | 5/2008 | Stone et al. | | 2013/0006102 A1 | 1/2013 | Wilkes et al. |
| 2008/0139944 A1 | 6/2008 | Weymer et al. | | | | |
| 2008/0146939 A1 | 6/2008 | McMorrow et al. | | | FOREIGN PATENT DOCUMENTS | |
| 2008/0146940 A1 | 6/2008 | Jenkins et al. | | | | |
| 2008/0154100 A1 | 6/2008 | Thalmeier et al. | | AU | 20009592 | 9/2000 |
| 2008/0166453 A1 | 7/2008 | Steele et al. | | AU | 20015250 | 6/2001 |
| 2008/0171934 A1 | 7/2008 | Greenan et al. | | AU | 768362 B2 | 12/2003 |
| 2008/0183075 A1 | 7/2008 | Govari et al. | | AU | 2001229024 B2 | 9/2005 |
| 2008/0200754 A1 | 8/2008 | Buchalter | | AU | 2001283703 B2 | 5/2006 |
| 2008/0228082 A1 | 9/2008 | Scheirer et al. | | AU | 2006202149 | 6/2006 |
| 2008/0255404 A1 | 10/2008 | Nogawa et al. | | AU | 2006904933 | 9/2006 |
| 2008/0255475 A1 | 10/2008 | Kondrosky et al. | | AU | 2006283022 B2 | 2/2012 |
| 2008/0275765 A1 | 11/2008 | Kuchar | | CA | 2420676 | 2/2002 |
| 2009/0005675 A1 | 1/2009 | Grunwald et al. | | CN | 102209490 A | 10/2011 |
| 2009/0018497 A1 | 1/2009 | Birchard et al. | | CN | 102802514 A | 11/2012 |
| 2009/0024018 A1 | 1/2009 | Boyden et al. | | CN | 102821679 A | 12/2012 |
| | | | | DE | 4319033 C1 | 6/1994 |

| | | |
|---|---|---|
| EP | 0359697 | 3/1990 |
| EP | 0362821 | 4/1990 |
| EP | 0399536 A1 | 11/1990 |
| EP | 0823261 A2 | 2/1998 |
| EP | 0928976 A2 | 7/1999 |
| EP | 1311226 A1 | 5/2003 |
| EP | 1504713 A1 | 2/2005 |
| EP | 2313143 A1 | 4/2011 |
| EP | 2440122 A1 | 4/2012 |
| EP | 2464407 A2 | 6/2012 |
| EP | 2482719 A1 | 8/2012 |
| FR | 2545349 | 11/1984 |
| JP | 01097440 | 4/1989 |
| JP | 03173542 A | 7/1991 |
| JP | 4090741 | 8/1992 |
| JP | 09-094298 A | 4/1997 |
| JP | 10043310 | 2/1998 |
| JP | 10290839 A | 11/1998 |
| JP | 11128237 A | 5/1999 |
| JP | 2001161683 | 6/2001 |
| JP | 2001340334 | 12/2001 |
| JP | 2003501127 A | 1/2003 |
| JP | 2003061752 A | 3/2003 |
| JP | 2003299654 | 10/2003 |
| JP | 2003334191 | 11/2003 |
| JP | 2002520893 | 2/2004 |
| JP | 2004505748 T | 2/2004 |
| JP | 2004515298 A | 5/2004 |
| JP | 2006508744 A | 3/2006 |
| JP | 5010604 | 6/2012 |
| JP | 2012-529929 | 11/2012 |
| WO | 9112836 A1 | 9/1991 |
| WO | 9203090 | 3/1992 |
| WO | 9403159 A1 | 2/1994 |
| WO | 9404938 | 3/1994 |
| WO | 9605768 A1 | 2/1996 |
| WO | 9607352 A1 | 3/1996 |
| WO | 9641119 | 12/1996 |
| WO | 9729683 A1 | 8/1997 |
| WO | 9743989 A1 | 11/1997 |
| WO | 9916495 A1 | 4/1999 |
| WO | 9949407 A1 | 9/1999 |
| WO | 0019906 | 4/2000 |
| WO | 0040155 | 7/2000 |
| WO | 0074775 A1 | 12/2000 |
| WO | 0176479 A1 | 10/2001 |
| WO | 0215973 A1 | 2/2002 |
| WO | 0225277 A1 | 3/2002 |
| WO | 03061752 | 7/2003 |
| WO | 03077759 A1 | 9/2003 |
| WO | 2004049970 A2 | 6/2004 |
| WO | 2005033524 A1 | 4/2005 |
| WO | 2005033574 A1 | 4/2005 |
| WO | 2005117690 A1 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 | 3/2008 |
| WO | 2008083111 | 7/2008 |
| WO | 2008118992 A1 | 10/2008 |
| WO | 2008126074 A2 | 10/2008 |
| WO | 2008131017 A2 | 10/2008 |
| WO | 2008136008 A2 | 11/2008 |
| WO | 2009002514 A2 | 12/2008 |
| WO | 2009009064 A1 | 1/2009 |
| WO | 2009057774 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010030820 A1 | 3/2010 |
| WO | 2010132857 A1 | 11/2010 |
| WO | 2010143196 A1 | 12/2010 |
| WO | 2010144922 A1 | 12/2010 |
| WO | 2011019760 A2 | 2/2011 |
| WO | 2011041450 A1 | 4/2011 |
| WO | 2011044421 A1 | 4/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2012021542 A2 | 2/2012 |
| WO | 2012024577 A2 | 2/2012 |
| WO | 2012058461 A1 | 5/2012 |
| WO | 2012083245 A1 | 6/2012 |
| WO | 2012088535 A1 | 6/2012 |
| WO | 2013006817 A1 | 1/2013 |

OTHER PUBLICATIONS

EP 09808901.4 filed Aug. 21, 2009 European Search Report dated May 23, 2012.
EP 09813632.8 filed Apr. 5, 2011 European Search Report dated Jul. 4, 2012.
Joosting, Jean-Pierre, "Dual-interface RFID-compatible EEPROM enables remote access to electronic device parameters," EE Times, Mar. 8, 2010.
JP 2010-504220 filed Sep. 3, 2009 Office Action dated May 21, 2012.
PCT/US2008/060502 filed Apr. 16, 2008 International Search Report and Written Opinion dated Oct. 16, 2008.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/048403 filed Aug. 19, 2011 International Search Report dated Dec. 15, 2011.
PCT/US2011/048403 filed Aug. 19, 2011 Written Opinion dated Dec. 15, 2011.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/557,401, filed Sep. 10, 2009 Non-Final Office Action dated Apr. 24, 2012.
"ASCENSION to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.

Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.

Arai, J et al, Detection of Peripherally Inserted Central Catheter Occlusion by in-line Pressure Monitoring, Paediatr Anaesth, pp. 621-624, vol. 12 No. 7, Sep. 2002.

Arrow International, Inc., The Arrow-Johans RAECG Adapter-Making Proper Central Venous Catheter Placement More Reliable (Modle No. EG-04900), Technical Report 1987, USA.

Aslamy, et al. "MRI of Central Venous Anatomy: Implications for Central Venous Catheter Insertion." American College of Chest Physicians, Jun. 8, 2009.

AU 2006283022 filed Aug. 24, 2006 Office Action dated Dec. 22, 2010.

AURORA® System Technical Specifications 2004.

B. Braun Website, "The Optimal Position of the Central Venous Catheter." http://www.cvcpartner.com/index.cfm18F1BDEA1310466194960A39F4E90968 (2009).

B. Braun, Certofix Central Venous Catheter for Placement Using the Seldinger Technique with Simultaneous ECG Lead Option. Feb. 2010.

Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.

Bankier, Alexander A., Azygos Arch Cannulation by Central Venous Catheters: Radiographic Detection of Malposition and Subsequent Complications, Journal of Thoracic Imaging 12:64-69 (1997).

Barber, JM et al, A Nurse led Peripherally Inserted Central Catheter Line Insertion Service is Effective with Radiological Support, Clin Radiol, pp. 352-354, vol. 57 No. 5, May 2002.

Bard Access Systems, Sherlock Tip Location System, 5 pages, 2006.

Bard Access Systems, Site Rite Vascular Acess Ultrasound System, 4 pages, 2005.

Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.

BioAdvance Lumen Vu, Greenhouse Fund Feb. 2004 Recipient, www.bioadvance.com <http://www.bioadvance.com>, 2005.

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

Buehrle, Douglas, PICC Placement in Humans using Electromagnetic Detection, <http://www.corpakmedsystems.com/supplement_material/supplementpages/navigator/navarticle.html>, 2008.

C.R. Bard, CathTrack™ Catheter Location System at www.bardaccess.com <http://www.bardaccess.com>, last accessed Apr. 28, 2011.

C.R. Bard, Inc., Bard Electrophysiology Product Catalogue, Bard Catheters, pp. 74-75 (2002), USA.

Cadman, A et al, To Clot or Not to Clot? That is the question in Central Venous Catheters, Clinical Radiology, pp. 349-355, vol. 59 No. 4, Apr. 2004.

Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.

Cardella, John F. et al., Interventinal Radiologic Placement of Peripherally Inserted Central Catheters, Journal of Vascular and Interventional Radiology 1993; 4:653-660.

Carlon, R et al, Secondary Migration of a Central Venous Catheter—A Case Report, Minerva Anestesiol, pp. 927-931, vol. 69 No. 12, Dec. 2003.

Caruso, LJ et al, A Better Landmark for Positioning a Central Venous Catheter, J Clinical Monitoring and Computing, pp. 331-334, vol. 17 No. 6, Aug. 2002.

Cavatorta, et al., "Central Venous Catheter Placement in Hemodialysis: Evaluation of Electrocardiography Using a Guidewire." The Journal of Vascular Access, vol. 2, pp. 45-50, 2001.

Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.

Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.

Chang, Thomas C. et al., Are Routine Ch Ladiographs Necessary After Image-Guided Placement of Internal Jugular Central Venous Access Devices?, AJR Feb. 1998;170:335-337.

Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.

Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.

Cheng, KI et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).

Cheung, P., et al., The Effect of a Disposable Probe Cover on Pulse Oximetry, Anaesth Intensive Care 2002; 30:211-214.

Chu, et al., "Accurate Central Venous Port—A Catheter Placement: Intravenous Electrocardiography and Surface Landmark Techniques Compared by Using Transesophageal Echocardiography." The International Anesthesia Research Society, vol. 98, pp. 910-914, 2004.

Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.

Clifford, et al. "Assessment of Hepatic Motion Secondary to Respiration for Computer Assisted Interventions." Computer Aided Surgery, vol. 7, pp. 291-299, 2002.

Colley, Peter S et al, ECG-Guided Placement of Sorenson CVP Catheters via Arm Veins, Anesthesia and Analgesia, pp. 953-956, vol. 63, 1984.

Collier, PE et al, Cardiac Tamponade from Central Venous Catheters, Am J Surg, pp. 212-214, vol. 176 No. 2, Aug. 1998.

ComboWire® Pressure/Flow Guide Wire Ref 9500 Series, 36 pages, (information in different languages), Apr. 2011.

Corsten, et al., "Central Placement Catheter Placement Using the ECG-Guided Cavafix-Certodyn SD Catheter." Journal of Clinical Anesthesiology, vol. 6, Nov./Dec. 1994.

Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.

Cullinane, DC et al, The Futility of Chest Roentgenograms Following Routine Central Venous Line Changes, Am J Surg, pp. 283-285, vol. 176 No. 3, Sep. 1998.

Curet, Myriam J. et al., University and Practice-based Physicians' Input on the Content of a Surgical Curriculum, The American Journal of Surgery® vol. 178 Jul. 1999, 78-84.

David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.

DELTEC Cath-Finder® Tracking System Operation Manual, 1994.

Yoon, SZ et al, Usefulness of the Carina as a Radiographic Landmark for Central Venous Catheter Placement in Paediatric Patients, Br J Anaesth, Jul. 2005.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.

Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.

Zachariou, Zacharias et al., Intra-atrial ECG recording: a new and safe method for implantation of Broviac catheters in children, Pediatr Surg Int (1994) 9: 457-458.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David Set al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
STEREOTAXIS Magetic Navigation System with Navigant™ User Interface, 2005 Brochure.
STEREOTAXIS, Expanding the Possibilites of Interventional Medicine: Remote Navigation and Automation, pp. 1-8, Apr. 2011.

Tepa® Health Innovation PC based ECG System Introduction and Technical Specifications, EKG Master USB, 2 pages, Nov. 2003.
The FloWire Doppler Guide Wire located <http://www.volcanocorp.com/products/flowire-doppler-guide-wire.php>, 2011.
TRAXAL Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Non-Final Office Action dated Sep. 25, 2009.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/369,625, filed Feb. 11, 2009 Final Office Action dated Feb. 23, 2012.
U.S. Appl. No. 12/369,625, filed Feb. 11, 2009 Non-Final Office Action dated Jul. 20, 2011.
U.S. Appl. No. 12/427,244, filed Apr. 21, 2009 Non-Final Office Action dated Jan. 19, 2012.
Valdivieso, J.R. Perez, et al., Evaluation of a formula for optimal positioning of a central venous catheter inserted through the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak © Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
NEUROMETER® CPT, Clinical Applications. Neurotron , Inc. website: www.neurotron.com/CLINAPS.html, last accessed Oct. 23, 2006.
NEUROMETER® CPT, Frequently Asked Questions. Neurotron , Inc. website: www.neurotron.com/CPTFAQ/html, last accessed Oct. 23, 2006.
NEUROMETER® CPT, Products Page. Neurotron , Inc. website: www.neurotron.com/products.html, last accessed Oct. 23, 2006.
NEUROMETER® Electrodiagnostic Neuroselective Sensory Nerve Evaluation: Charts, Tables, Documents & Downloads. Neurotron , Inc. website: www.neurotron.com/downloads.html, last accessed Oct. 23, 2006.

Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid col. Electrocardiograms." European Journal of Anaesthesiology, vol. 41, pp. 594-599, 2004.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/067268 filed Dec. 23, 2011 International Search Report and Written Opinion dated Apr. 27, 2012.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Popp, M. B. et al., Accuracy of implanted port placement with the use of the electromagnetic CathTrack® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Intery Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, the Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.

Gonzales, et al. "Peripherally Inserted Central Catheter Placement in Swine Using Magnet Detection." Journal of Intravenous Nursing, vol. 22, No. 3, May/Jun. 1999.

Greenall, M.J. et al, Cardiac Tamponade and Central Venous Catheters, British Medical Journal, pp. 595-597, Jun. 14, 1975.

Guillory, "Basic Principles of Technologies for Catheter Localization." C.R. Bard internal paper, Oct. 20, 2004.

Guth, AA, Routine Chest X-rays after Insertion of Implantable Long-Term Venous Catheters: Necessary or Not?, Am Surg, pp. 26-29, vol. 67 No. 1, Jan. 2001 (Abstract only).

Hill, Bradley et al, Abstract of article discussing Vasallova VPS as guide for placement of PICCs. 2009.

Hill, Bradley, Identifying the Caval-Atrial Junction Using Smart-Catheter Technology presentation, 22nd Annual Scientific Meeting of the AVA in Savannah, Georgia, Sep. 13, 2008.

Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.

Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.

JP 2008-528151 filed Aug. 24, 2006 Notice of Grant dated May 6, 2012.

Kim, Ko et al, Positioning Internal Jugular Venous Catheters using the Right Third Intercostal Space in Children, Acta Anaesthesiol Scand, pp. 1284-1286, vol. 47 No. 10, Nov. 2003.

Kjelstrup T et al, Positioning of Central Venous Catheters using ECG, Tidssk nor Laegeforen, pp. 599-601, vol. 111 No. 5, Feb. 1999 (Abstract only).

Kofler, Julia, et al., Epinephrine application via an endotracheal airway and via the Combitube in esophageal position, Critical Care Medicine: May 2000, vol. 28: Issue 5, pp. 1445-1449.

Kowalski, CM et al, Migration of Central Venous Catheters: Implications for Initial Catheter Tip Positioning, J Vasc Intery Radiol, pp. 443-447, vol. 8 No. 3, May-Jun. 1997.

Leowenthal, MR et al, the Peripherally Inserted Central Catheter (PICC): A Prospective Study of its Natural History after Fossa Insertion, Anaesth Intensive Care, pp. 21-24; vol. 30 No. 1, Feb. 2002.

Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.

Liu , Ji-Bin et al, Catheter-Based Intraluminal Sonography, J Ultrasound Med, pp. 145-160, vol. 23, 2004.

Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.

Lum, Phillip, A New Formula-Based Measurement Guide for Optimal Positioning of Central Venous Catheters, JAVA, vol. 9, No. 2, pp. 80-85, 2004.

Lynch, RE et al, A Procedure for Placing Pediatric Femoral Venous Catheter Tips near the Right Atrium, Pediatr Emerg Care, pp. 130-132, vol. 18 No. 2, Apr. 2002.

Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.

Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.

Markovich, Mary B., Central Venous Catheter Tip Placement: Determination of Posterior Malposition—A Case Study, Java, vol. 11, No. 2, pp. 85-89, 2006.

Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.

McDonnall, "Intra-Atrial Electrocardiography (ECG) for Catheter Placement." Literature review prepared for Bard Access Systems, Oct. 2007.

McGee et al., "Accurate Placement of Central Venous Catheters: A Prospective, Randomize, Multicenter Trail." Critical Care Medicine, vol. 21 No. 8, Aug. 1993.

MedGraphics, CardioPerfect® Resting/Stress ECG System, 3 pages, 2001.

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.

Michenfelder, John et al, Air Embolism During Neurosurgery. A New Method of Treatment, Anesthesia and Analgesia. Current Researches, pp. 390-395, vol. 45, No. 4, Jul.-Aug. 1966.

MICROBIRD™ Miniaturized DC Magnetic Sensors for Intra-body Navigation and Localization, Specifications, 2005.

MICRONIX CathRite™ Cardiac Access Device Brochure. Jun. 2004.

Micronix Pty Ltd "CathRite" Guiding Styled Core Manufacturing, Jun. 15, 2006.

Murthy, Vrudhula et al, Analysis of Power Spectral Densities of Electrocardiograms, Mathematical Biosciences, pp. 41-51, vol. 12 No. 1-2, Oct. 1971.

Nadroo, AM et al, Changes in Upper Extremity Position Cause Migration of Peripherally Inserted Central Catheters in Neonates, Pediatrics, pp. 131-136, vol. 110, Jul. 2002.

Nakatani, K et al, Accurate Placement of Central Venous Catheters—ECG-guided method vs Patient Height Method, Masui, pp. 34-38, vol. 51 No. 1, Jan. 2002.

Nazarian, GK et al, Changes in Tunneled Catheter Tip Position when a patient is Upright, J Vasc Intery Radio!, pp. 437-441, vol. 8 No. 3, May-Jun. 1997.

AU 2008329807 exam requested Aug. 13, 2012 Examination Report No. 1 dated Feb. 15, 2013.

CA 2,619,909 filed Aug. 24, 2006 Examiner's Report dated Oct. 26, 2012.

CN 200880012117.4 filed Apr. 16, 2008 Second Office Action dated Oct. 8, 2012.

CN 200880125528.4 filed Nov. 25, 2008 First Office Action dated Jun. 5, 2012.

CN 200980123021.X filed Dec. 17, 2010 First Office Action dated Nov. 19, 2012.

EP 08855396.1 filed Jun. 15, 2010 European Search Report dated Jul. 31, 2012.

EP 12177438.4 filed Jul. 23, 2012 European Search Report dated Dec. 4, 2012.

Konings, MK, et al., Development of an intravascular impedance catheter for detection of fatty lesions in arteries, IEEE Trans Med Imaging Aug. 1997; 16(4):439-46.

PCT/US2011/038391 filed May 27, 2011 International Preliminary Report on Patentability and Written Opinion dated Dec. 4, 2012.

PCT/US2011/038391 filed May 27, 2011 International Search Report dated Sep. 21, 2011.

PCT/US2011/038415 filed May 27, 2011 International Preliminary Report on Patentability dated Dec. 13, 2012.

PCT/US2011/058138 filed Oct. 27, 2011 International Search Report dated Feb. 7, 2012.

PCT/US2011/058138 filed Oct. 27, 2011 Written Opinion dated Feb. 7, 2012.

PCT/US2012/045814 filed Jul. 6, 2012 International Search Report and Written Opinion dated Oct. 1, 2012.

Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.

U.S. Appl. No. 11/466,602 filed Aug. 23, 2006 Appeal Board Decision dated Sep. 17, 2012.

U.S. Appl. No. 11/466,602 filed Aug. 23, 2006 Notice of Allowance dated Dec. 3, 2012.

U.S. Appl. No. 12/369,625 filed Feb. 11, 2009 Notice of Allowance dated Oct. 5, 2012.
U.S. Appl. No. 12/369,625 filed Feb. 11, 2009 Notice of Panel Decision dated Aug. 1, 2012.
U.S. Appl. No. 12/426,175 filed Apr. 17, 2009 Non-Final Office Action dated Dec. 3, 2012.
U.S. Appl. No. 12/545,762 filed Aug. 21, 2009 Non-Final Office Action dated Aug. 1, 2012.
U.S. Appl. No. 12/575,456 filed Oct. 7, 2009 Non-Final Office Action dated Oct. 5, 2012.
U.S. Appl. No. 12/715,556 filed Mar. 2, 2010 Non-Final Office Action dated Sep. 13, 2012.
U.S. Appl. No. 12/854,083 filed Aug. 10, 2010 Non-Final Office Action dated Jan. 29, 2013.
U.S. Appl. No. 13/118,138 filed May 27, 2011 Non-Final Office Action dated Oct. 3, 2012.
U.S. Appl. No. 13/213,622 filed Aug. 19, 2011 Non-Final Office Action dated Jul. 31, 2012.
U.S. Appl. No. 13/336,919 filed Dec. 23, 2011 Non-Final Office Action dated Oct. 16, 2012.

* cited by examiner

METHOD OF LOCATING THE TIP OF A CENTRAL VENOUS CATHETER

PRIORITY

This application is a division of U.S. patent application Ser. No. 11/552,094, filed Oct. 23, 2006, now U.S. Pat. No. 7,794,407, which is incorporated by reference into this application as if fully set forth herein.

BACKGROUND OF THE INVENTION

1. Field of the Invention

The present invention is directed generally to devices for and methods of locating a catheter inside a body and more particularly to devices for and methods of locating the tip of a central venous catheter inside the superior vena cava, right atrium, and/or right ventricle using information obtained from an electrocardiogram.

2. Description of the Related Art

Central venous catheters ("CVC") include any catheter designed to utilize the central veins (e.g., subclavian and superior vena cava) or right sided cardiac chambers for the delivery and/or withdrawal of blood, blood products, therapeutic agents, and/or diagnostic agents. CVCs also include catheters inserted into the central veins or right sided cardiac chambers for the acquisition of hemodynamic data. Standard central venous catheters for intravenous access, dialysis catheters, percutaneously introduced central catheters ("PICC" lines), and right heart ("Swan-Ganz™") catheters are examples of CVCs.

The standard of care for placing a CVC dictates that the tip of the CVC lie just above and not inside the right atrium. In fact, in 1989, the Food and Drug Administration issued a warning citing an increased risk of perforation of the right atrium, clot formation, and arrhythmias among other potential complications resulting from the tip of the CVC being placed inside the right atrium.

While CVCs have been used for many years, determining the position of the tip of the CVC has always been problematic. Currently, a chest x-ray is used to determine the position of the tip of the CVC. Because CVC may be a radiopaque and/or include radiopaque materials, the CVC is visible on an x-ray. However, this method has several drawbacks. For example, obtaining a chest x-ray is labor intensive and expensive. In recent years, CVCs, which were traditionally placed in a hospital in-patient setting, are being placed in an outpatient setting more frequently. In an outpatient setting, obtaining a chest x-ray to determine the position of the tip of the CVC can be very cumbersome and may not be obtained in a timely manner. Therefore, using a chest x-ray to determine the position of the tip of the CVC may introduce a considerable delay, prolonging the procedure. Generally, the operator will leave the patient to perform other duties while the x-ray is processed. If the tip is improperly placed, the operator must return to the patient's bedside to reposition the CVC. To reposition the CVC, the operator must open the sterile dressing, cut the sutures, re-suture, and redress the wound, all of which potentially expose the patient to discomfort and infection.

In addition to the need to know where the tip is during initial placement, the CVC may migrate or otherwise move after the initial placement and require re-positioning. Therefore, the operator must monitor or periodically reevaluate the location of the tip.

An electrocardiogram (ECG) measures electrical potential changes occurring in the heart. Referring to FIGS. 1A-1C, the ECG measurements may be visualized or displayed as an ECG trace, which includes ECG waveforms. The P wave portion of the ECG waveforms represents atrial muscle depolarization: the first half is attributable to the right atrium and the second half to the left atrium. Under normal circumstances, atrial muscle depolarization is initiated by a release of an excitatory signal from the sino-atrial node, a specialized strip of tissue located at the juncture of the superior vena cava ("SVC") and right atrium.

Techniques of using ECG waveforms to locate the tip of a CVC have been available since the 1940's. Some of these prior art devices construct an intravascular ECG trace by placing an electrode near the tip of the CVC and using that electrode to measure the voltage near the tip of the CVC relative to a surface electrode(s) and/or a second electrode spaced from the first.

These techniques have shown that both the magnitude and shape of the P wave change depending upon the positioning or location of the electrode attached to the tip of the CVC. Referring to FIGS. 1A and 1B, two exemplary ECG traces are provided for illustrative purposes.

FIG. 1A is an ECG trace made when the electrode attached to tip of the CVC is in the SVC. This tip location corresponds to position "1" depicted in FIG. 2A. The portion of the ECG trace corresponding to an exemplary P wave produced when the electrode attached to the tip is located in position "1" is labeled "P1."

FIG. 1B is an ECG trace made when the electrode attached to the tip of the CVC is approaching the sino-atrial node and stops at a location adjacent to the sino-atrial node. These tip locations correspond to moving the tip from a position "2" to position "3" depicted in FIG. 2A. The portion of the ECG trace corresponding to an exemplary P wave produced when the electrode attached to the tip is approaching the sino-atrial node is labeled "P2" and the portion of the ECG trace corresponding to an exemplary P wave produced when the electrode attached to the tip is located adjacent to the sino-atrial node is labeled "P3."

Normally as the electrode attached to the tip of the CVC moves from the SVC (position "1") toward the sino-atrial node (position "3"), the maximum value of the absolute value of the voltage of the P wave increases dramatically. When the electrode attached to tip of the CVC is adjacent to the sino-atrial node (position "3"), the voltage of the P wave (please see "P3" of FIG. 1B) reaches a maximum value that is more than twice the value experienced in the SVC and may be as large as eight times the voltage in the SVC. When this occurs, the tip of the CVC is considered to have entered into the right atrium. Because the magnitude of the P wave more than doubles when the electrode attached to tip of the CVC is adjacent to the sino-atrial node, this information may be used to place the tip of the CVC within 1-2 cm proximal to the sino-atrial node. Additionally, as the electrode attached to tip of the CVC moves from the SVC toward the right atrium, the shape of the P wave changes from a "u" shape (FIG. 1A) to a spike-like shape (FIG. 1B).

Referring to FIG. 2B, another exemplary illustration of the P wave portion of the ECG trace produced when the electrode attached to the tip of the CVC is located at positions 1-5 depicted in FIG. 2A is provided. The P wave portions of the ECG traces of FIG. 2B are labeled with the letter "P" and occur between the vertical dashed lines. Each of the exemplary traces is numbered to correspond to positions "1" through "5." Therefore, the ECG trace "1" was produced when the electrode attached to the tip was located in the SVC. The trace "2" was produced when the electrode attached to the tip was in position "2." And, the trace "3" was produced when the electrode attached to the tip was adjacent to the sino-atrial node.

As the electrode attached to tip of the CVC is advanced further into the right atrium, the polarity of the P wave "P" changes from predominantly negative near the top of the right atrium (position "3") to isoelectric (i.e., half has a positive polarity and half has a negative polarity) near the middle of the right atrium (position "4") to almost entirely positive at the bottom of the right atrium (position "5"). These changes in the P wave "P" are illustrated in traces "3" through "5."

FIG. 1C is an ECG trace made when the electrode attached to tip of the CVC is in the right ventricle. The portion of the ECG trace corresponding to an exemplary P wave produced when the electrode attached to the tip is labeled "P6." When the electrode attached to tip of the CVC is advanced into the right ventricle, the maximum magnitude of the absolute value of the P wave "P6" approximates the maximum magnitude of the absolute value of the P wave "P1" when the electrode attached to tip of the CVC was inside the SVC above the sino-atrial node (i.e., located at position "1"). However, the polarity of the first half of P wave "P6," which corresponds to the right atrium, is opposite.

The first technique developed for viewing the ECG waveform during the insertion of a CVC used a column of saline disposed within a hollow tube or lumen longitudinally traversing the CVC. The column of saline provides a conductive medium. Saline was inserted into the lumen by a saline filled syringe with a metal needle. The needle of the syringe remained within the entrance to the lumen or port in contact with the column of saline after the lumen was filled. One end of a double-sided alligator clip was attached to the needle and the other end was attached to an ECG lead, which in turn was attached to an ECG monitor. By using the saline solution filled CVC as a unipolar electrode and a second virtual electrode generated by ECG software from three surface electrodes, an intravascular ECG was obtained. The operator would adjust the position of the tip of the CVC based on the magnitude and shape of the P wave displayed by the ECG monitor.

Subsequently, this technique was modified by substituting an Arrow-Johans adapter for the metal needle. The Arrow-Johans adapter is a standard tubing connector with a embedded conductive ECG eyelet. The Arrow-Johans adapter may be placed in line with any conventional CVC. In a closed system, the tubing and CVC may be filled with saline, i.e., a conductive medium, and the CVC used as a unipolar electrode in conjunction with surface electrodes and a standard ECG monitor. The ECG eyelet is placed in contact with the saline in the lumen of the CVC. One end of the ECG lead is attached to the ECG eyelet and the other end to the ECG monitor for displaying the intravascular ECG waveforms. Because the system must be closed to prevent the saline from leaking out, this system works best after the guide wire used to thread the CVC forward has been withdrawn, i.e., after placement has been completed. Therefore, although the catheter may be withdrawn after initial placement, it may not be advanced into proper position.

BBraun introduced its Certofix catheter to be used in conjunction with its Certodyne adapter. In this system, a patch lead with two ends has an alligator clip connected to one end. The alligator clip is clipped to the CVC guide wire. The other end of the patch lead includes a connector that is plugged into the Certodyne adapter. The ECG may be obtained during placement and the catheter may be advanced or withdrawn as desired. However, the Certodyne adapter has many moving parts and is not sterile, making the procedure cumbersome to perform and the operative field more congested. Additionally, the sterile field may become contaminated by the non-sterile equipment.

With respect to all of these prior art methods of using an ECG trace to place the tip of the CVC, some degree of expertise is required to interpret the P waves measured because the user must advance the guide wire slowly and watch for changes in the P wave. If the catheter is inserted too far too quickly and the changes to the P wave go unnoticed (i.e., the operator fails to notice the increase or spike in the voltage experienced when the electrode attached to the tip is in the right atrium), the operator may mistakenly believe the tip is in the SVC when, in fact, the tip is in the right ventricle. If this occurs, advancing the tip may injure the patient.

U.S. Pat. Nos. 5,078,678 and 5,121,750 both issued to Katims teach a method of using the P wave portion of an ECG trace to guide placement of the tip of the CVC. The CVC includes two empty lumens into which a transmission line is fed or an electrolyte is added. Each of the lumens has a distal exit aperture located near the tip of the CVC. The two exit apertures are spaced from one another. In this manner, two spaced apart electrodes or a single anode/cathode pair are constructed near the tip of the CVC. The voltage or potential of one of the electrodes relative to the other varies depending upon the placement of the electrodes. The voltage of the electrodes is conducted to a catheter monitoring system. The catheter monitoring system detects increases and decreases in the voltage of the P wave. The voltage increases as the electrodes approach the sino-atrial node and decrease as the electrodes move away from the sino-atrial node. Based on whether the voltage is increasing or decreasing, the operator is instructed by messages on a screen to advance or withdraw the CVC.

While Katims teaches a method of locating the tip of a CVC relative to the sino-atrial node, Katims relies on advancing or withdrawing the CVC and observing the changes of the P wave. Katims does not disclose a method of determining the location of the tip of the CVC based on a single stationary position. Unless the entire insertion procedure is monitored carefully, the method cannot determine the position of the tip of the CVC. Further, the Katims method may be unsuitable for determining the location of a previously positioned stationary tip.

Other devices such as Bard's Zucker, Myler, Gorlin, and CVP/Pacing Lumen Electrode Catheters are designed primarily to pace. These devices include a pair of electrodes at their tip that are permanently installed and designed to contact the endocardial lining. These devices include a lumen, which may be used to deliver and/or withdraw medications or fluids as well as for pressure monitoring. These leads are not designed for tip location and do not include multi-lumen capability.

A method of obtaining an intravascular ECG for the purposes of placing a temporary pacing wire was described in U.S. Pat. No. 5,666,958 issued to Rothenberg et. al. Rothenberg et. al discloses a bipolar pacing wire having a distal electrode. The distal electrode serves as a unipolar electrode when the pacing wire is inserted into the chambers of the heart. The pacing wire is connected to a bedside monitor through a specialized connector for the purposes of displaying the ECG waveforms detected by the distal electrode.

Given the volume of CVCs placed yearly and the increasing demand particularly for PICC lines (devices that permit the delivery of intravenous therapeutic agents in the outpatient setting, avoiding the need for hospitalization) a great need exists for methods and devices related to locating the tip of a CVC. Particularly, devices and methods are needed that are capable of determining the location of the tip before the operator leaves the bedside of the patient. Further, a method of determining the location (SVC, right atrium, or right ventricle) of the tip from a single data point rather than from a series of data points collected as the catheter is moved may be advantageous. Such a system may be helpful during initial placement and/or repositioning. A need also exists for a device for or a method of interpreting the ECG waveforms that does not require specialized expertise. Methods and devices that avoid the need for hospital and x-ray facilities are also desirable. A need also exists for devices and methods related to determining the position of the tip of the CVC that are less expensive, expose patients to fewer risks, and/or are less cumbersome than the x-ray method currently in use.

BRIEF DESCRIPTION OF THE SEVERAL VIEWS OF THE DRAWING(S)

Figure 1A:
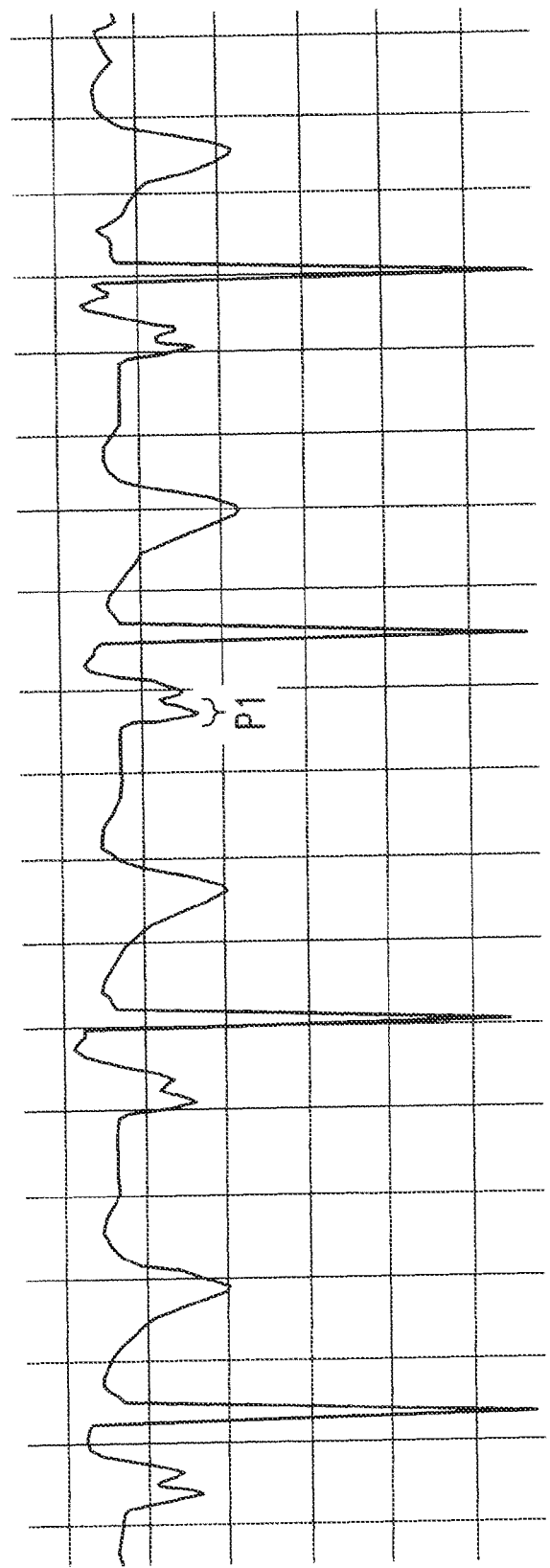
FIG. 1A is an exemplary ECG trace obtained from an electrode placed inside the SVC.
Figure 1B:
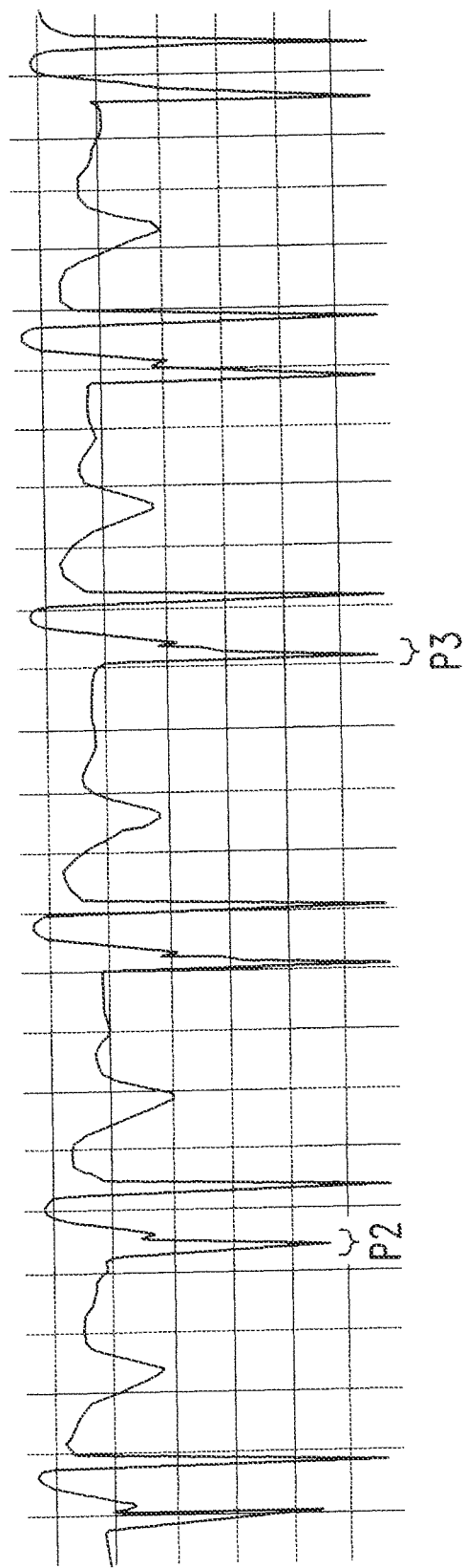
FIG. 1B is an exemplary ECG trace obtained from an electrode approaching the sino-atrial node and stopping adjacent thereto.
Figure 1C:
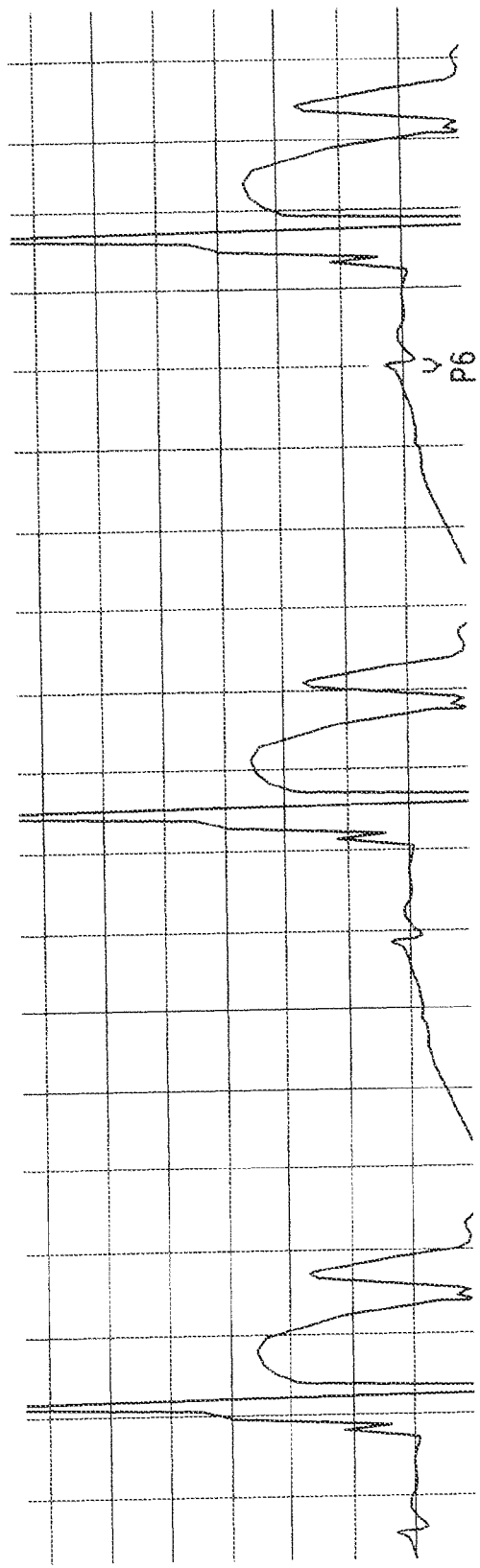
FIG. 1C is an exemplary ECG trace obtained from an electrode placed inside the right ventricle.
Figure 2B:
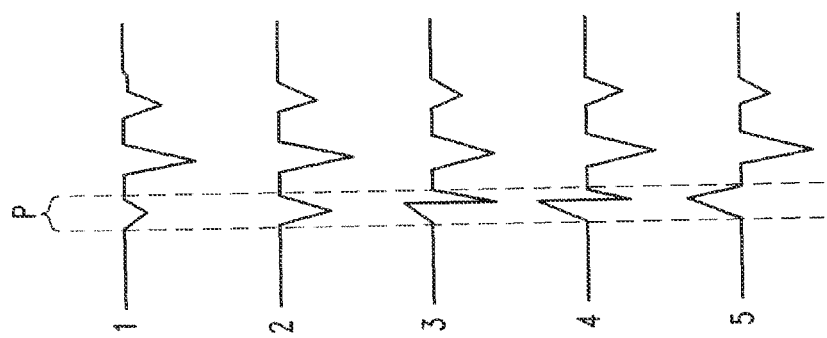
FIG. 2A is an illustration of a partial cross-section of the heart providing three exemplary tip locations 1, 2, 3, 4, and 5.
Figure 2A:
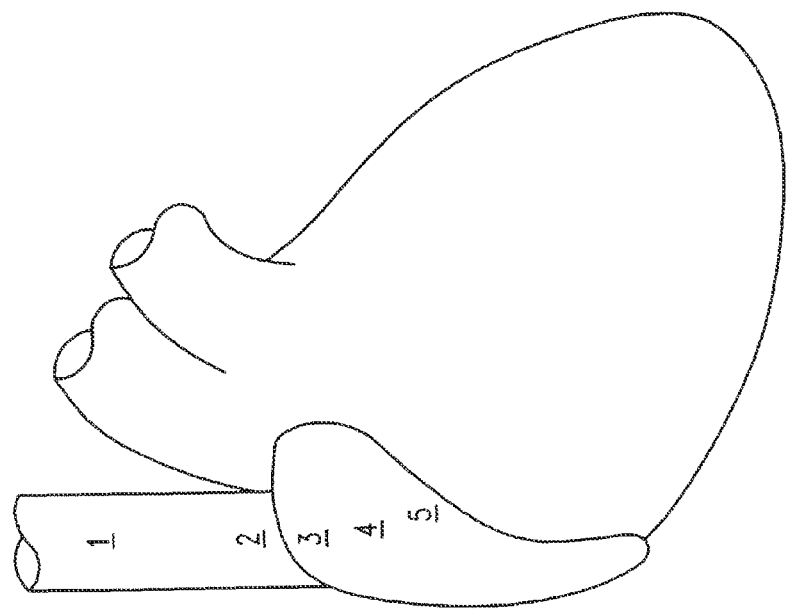

FIG. 2B is a series of exemplary P wave traces 1, 2, 3, 4, and 5 obtained from an electrode placed in each of the exemplary tip locations 1, 2, 3, 4, and 5 depicted in FIG. 2A, respectively.

Figure 3:
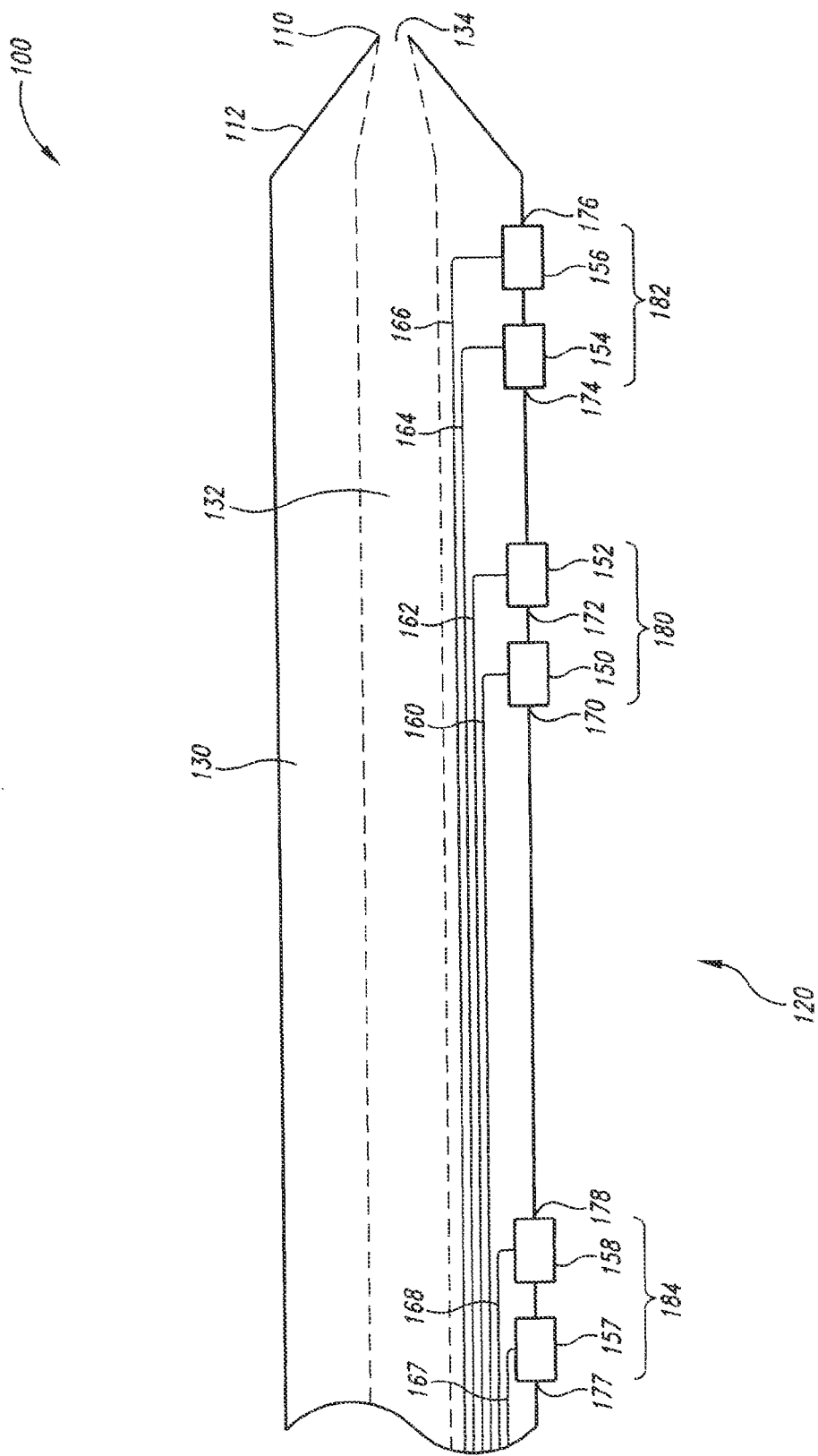

FIG. 3 is a CVC constructed in accordance with aspects of the present invention.

Figure 4:
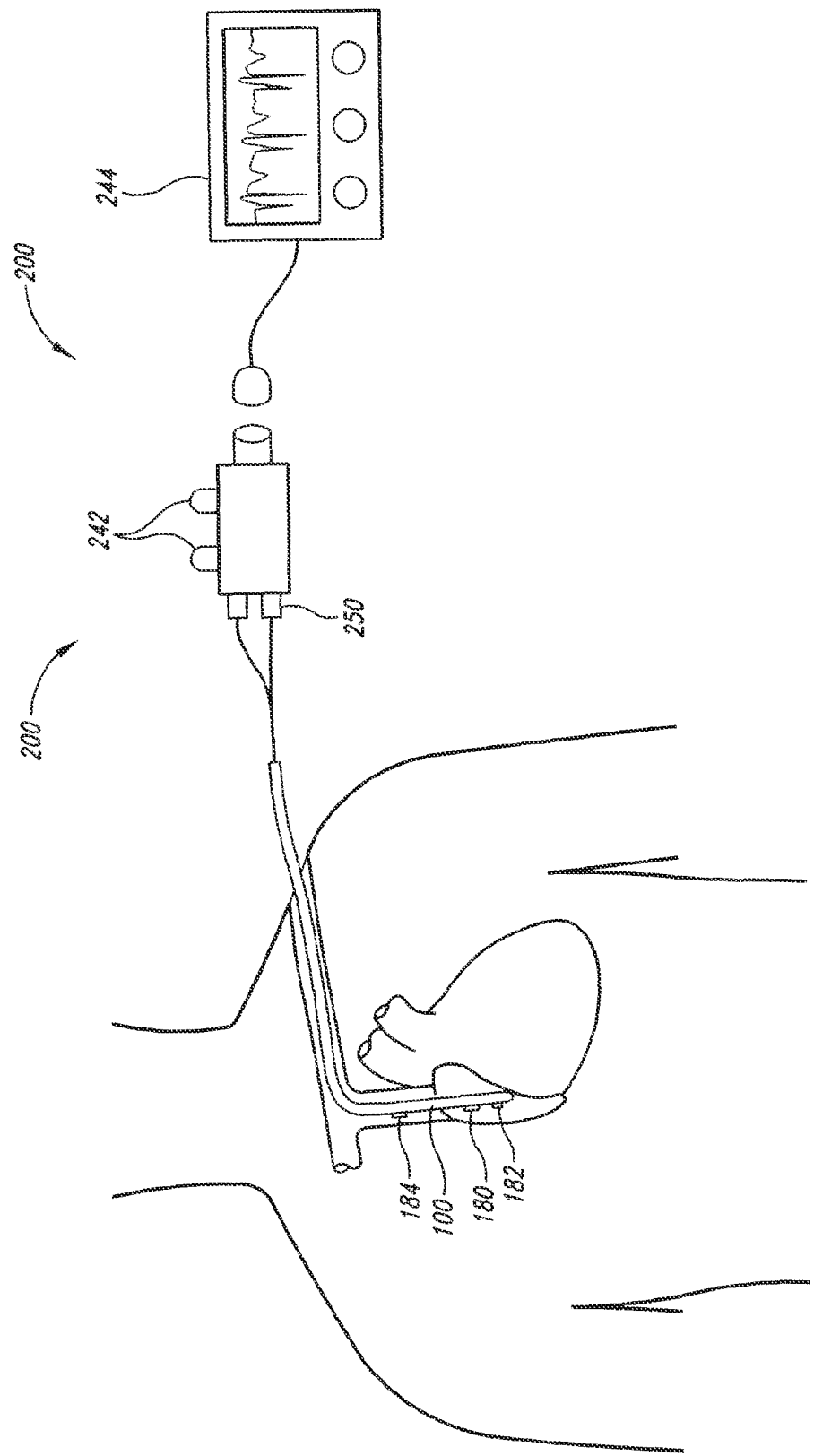

FIG. 4 is an embodiment of a signal analysis system for use with the CVC of FIG. 3.

Figure 5:
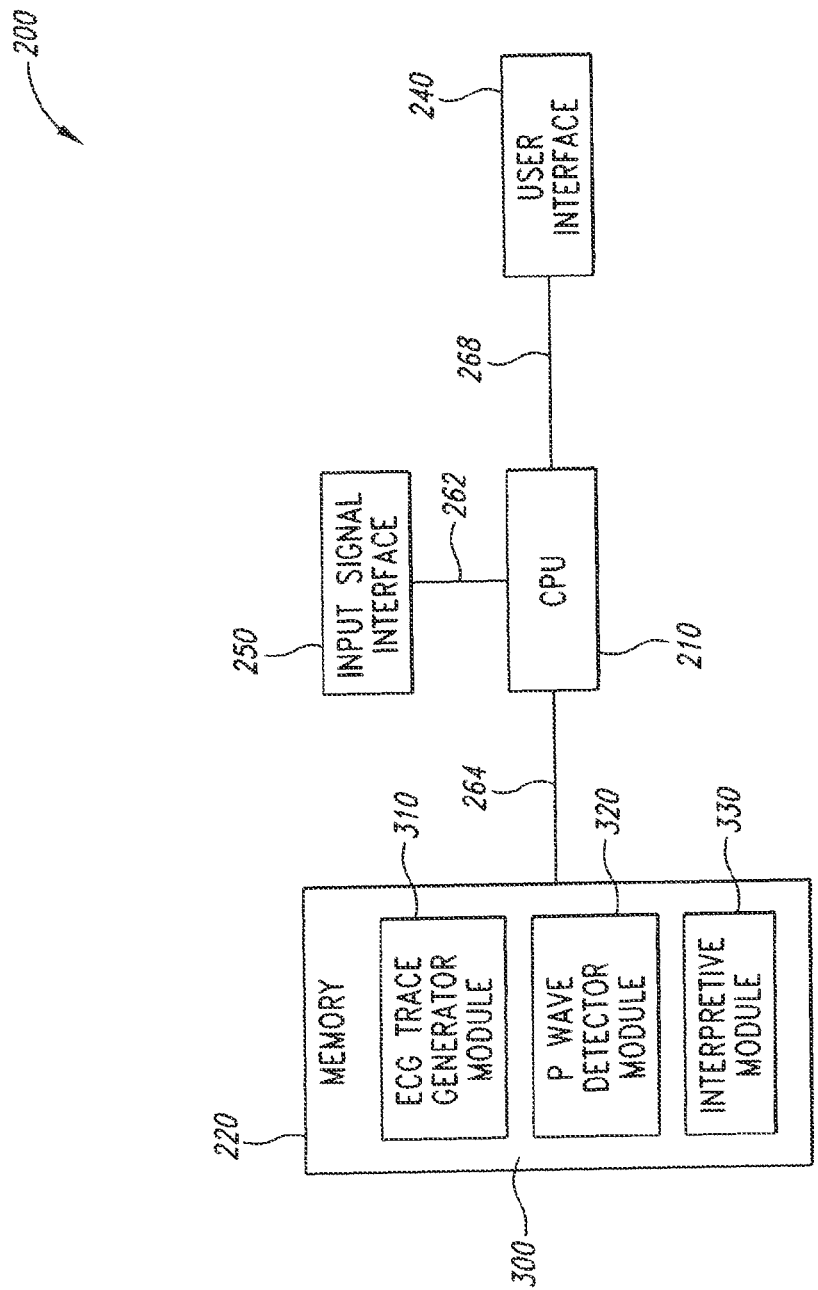

FIG. 5 is a block diagram illustrating the components of the signal analysis system of FIG. 4.

DETAILED DESCRIPTION OF THE INVENTION

Aspects of the present invention are directed toward a device for locating the tip of a CVC and a method of determining the location of the tip of a CVC. In the embodiment depicted in FIG. 3, the invention includes a CVC 100 constructed using any manner known in the art from a flexible nonconductive material, such as polyurethane or other suitable polymer material. It may also be desirable to use a radiopaque material. As is appreciated by those of ordinary skill in the art, the material used to construct the CVC 100 may include materials and/or coatings that provide improved anti-thrombotic or anti-bacterial properties. The CVC 100 has a body 130 configured to be received within a central vein. The body 130 may include a distal end 110 having a tapered tip 112 and a proximal end 120 spaced longitudinally along the body 130 from the distal end 110.

The body 130 may include one or more lumens 132 that traverse the length of the body and may have one or more openings 134 at or spaced from the tip 112. The openings 134 permit passage of material(s) between the lumen 132 and the environment outside the CVC 100. The lumens 132 may be used as conduits for the passage of materials such as medications and/or other fluids to and from the environment outside the CVC 100. For example, the lumen 132 may be used to aspirate blood into the CVC 100 and/or provide a conduit through which pressure data may be collected and used to construct pressure waveforms. The environment outside the CVC 100 may include the inside of the SVC, right atrium, and/or right ventricle. The CVC 100 is provided for illustrative purposes and those of ordinary skill in the art appreciate that alternate embodiments of CVC 100 including embodiments with additional lumens, a flow directed balloon tip, thermistors, thermodilution ports, pacing wire ports, embedded pacing electrodes, and the like are within the scope of the present invention.

In one embodiment, the invention includes four longitudinally spaced apart electrodes 150, 152, 154, and 156. Each electrode 150, 152, 154, and 156 is in electrical communication with a wire 160, 162, 164, and 166, respectively. In one embodiment, the electrodes 150, 152, 154, and 156 are constructed from the distal end of each of the wires 160, 162, 164, and 166. In another embodiment, the electrodes 150, 152, 154, and 156 are attached to the ends of the wires 160, 162, 164, and 166 by any method known in the art for attaching an electrode to a wire, including soldering. The wires 160, 162, 164, and 166 are electrically isolated from one another. The wires 160, 162, 164, and 166 may be insulated from the environment outside the body 130 by the body 130.

The electrodes 150, 152, 154, and 156 and the wires 160, 162, 164, and 166 may be constructed from any suitable materials known in the art such as stainless steel or platinum. The electrodes 150, 152, 154, and 156 may be about 6 mm to about 12 mm long, about 6 mm to about 12 mm wide, and about 1 mm to about 4 mm thick. The wires 160, 162, 164, and 166 may be constructed using any electrical lead wire suitable for obtaining an ECG trace.

Optionally, the invention may include two longitudinally spaced apart electrodes 157 and 158. Each of the electrodes 157 and 158 may be electrical communication with a wire 167 and 168, respectively. The electrodes 157 and 158 and wires 167 and 168 may be constructed in a manner substantially similar to that used to construct the electrodes 150, 152, 154, and 156 and the wires 160, 162, 164, and 166, respectively. In one embodiment, the electrode 157 and 158 are positioned proximal to the electrodes 150, 152, 154, and 156.

Electrodes 150, 152, 154, and 156 may form two anode/cathode pairs. For example, electrodes 150 and 152 may form a first or proximal anode/cathode pair 180 and electrodes 154 and 156 may form a second or distal anode/cathode pair 182. Optional electrodes 157 and 158 may form an optional third or reference anode/cathode pair 184. A pair of electrodes forming an anode/cathode pair may be attached to a pair of insulated wires housed within a single cable. In one embodiment, a pair of bipolar lead wires are used. In this manner, the four electrodes of the proximal and distal anode/cathode pairs 180 and 182 may be attached to two lead wires. A third bipolar lead wire may be included for use with the reference anode/cathode pair 184. Alternatively, the proximal and distal anode/cathode pairs 180 and 182 may be attached to four insulated wires housed within a single cable such a dual bipolar lead wire.

The wires 160, 162, 164, and 166 and electrodes 150, 152, 154, and 156 may be permanently embedded into the body 130 of the CVC 100 or removably inserted into one or more channels or lumens 132 formed in the CVC 100 for potential future removal and/or replacement. The wires 167 and 168 and electrodes 157 and 158 may be incorporated into the CVC 100 in any manner described with respect to wires 160, 162, 164, and 166 and electrodes 150, 152, 154, and 156, respectively.

The electrodes 150, 152, 154, and 156 are in electrical communication with the environment outside the CVC 100. In one embodiment, a portion of each of the electrodes 150, 152, 154, and 156 are exposed to the environment outside the CVC 100 by apertures 170, 172, 174, and 176 formed in the body 130 adjacent to the electrodes 150, 152, 154, and 156, respectively. In embodiments including optional electrodes 157 and 158, a portion of each of the electrodes 157 and 158 may be exposed to the environment outside the CVC 100 by apertures 177 and 178 formed in the body 130 adjacent to the electrodes 157 and 158, respectively. The apertures 177 and 178 may be constructed in any manner suitable for constructing apertures 170, 172, 174, and 176. The apertures 170, 172, 174, and 176 may be formed in the body 130 by any method known in the art and the invention is not limited by the method used to construct the apertures 170, 172, 174, and 176. While the electrodes 150, 152, 154, and 156 depicted in the drawings extend outwardly from the body 130 through the apertures 170, 172, 174, and 176, it is understood by those of ordinary skill in the art, that electrodes 150, 152, 154, and 156 may reside at the bottom of the apertures 170, 172, 174, and 176 which may provide a passageway for fluids in the outside environment to the electrodes 150, 152, 154, and 156. Alternatively, the portion of the electrodes 150, 152, 154, and 156 in electrical communication with the environment outside the CVC 100 may be flush with the outside surface of the CVC 100.

The electrode 156 may be located at or spaced from the tip 112. In one embodiment, the electrode 156 is less than about 5 mm from the tip 112. The spacing between an anode and cathode of the anode/cathode pairs 180 and 182 may be about 1 mm to about 4 mm. In one embodiment, the spacing between an anode and cathode of the anode/cathode pairs 180 and 182 is about 3 mm.

In one embodiment, the distance between the electrodes 154 and 152 is less than the height of the right atrium. In an adult, the height of the right atrium may be approximately equal to or greater than about 4 cm. In one exemplary embodiment, the distance between the electrode 154 and 152 may be about 3 cm. In embodiments including optional electrodes 157 and 158, the distance between the electrodes 150 and 158 may be about 10 cm to about 18 cm.

Those of ordinary skill in the art appreciate that the size and spacing of the electrodes provided herein may require modification for use with patients that are larger or smaller than a typical adult and such embodiments are within the scope of the present invention. For example, smaller electrodes with a closer spacing may be required for use with a pediatric patient.

Referring to FIG. 4, the CVC 100 may gain venous access to the SVC by any method known in the art including inserting the CVC 100 in a standard sterile fashion through the subclavian, one of the jugular veins, or a peripheral vein and directing the tip 112 of the CVC 100 through that vein to the SVC.

Each of the anode/cathode pairs 180 and 182 may be used to generate an ECG trace. In this manner, the ECG waveforms detected by the proximal pair 180 may be compared to the ECG waveform detected by the distal pair 182. In one embodiment, the P wave portion of each trace is compared to determine the position of the tip 112 of the CVC 100 within the SVC, right atrium, and right ventricle.

In embodiments including the reference anode/cathode pair 184, the reference anode/cathode pair 184 may be used to generate an ECG trace. Referring to FIG. 4, because the reference anode/cathode pairs 184 may be located substantially proximally from the proximal and distal anode/cathode pairs 180 and 182, the reference anode/cathode pair 184 may remain in the SVC after the proximal and distal anode/cathode pairs 180 and 182 have entered the heart. In one embodiment, the spacing between the anode/cathode pair 184 and the proximal pair 180 is large enough to insure the reference anode/cathode pair 184 remains inside the SVC when the distal anode/cathode pair 182 is inside the right ventricle. In this manner, the reference anode/cathode pair 184, may be used to detect the ECG waveform within the SVC while the catheter is being placed.

The ECG waveforms detected by the proximal anode/cathode pair 180 and/or distal anode/cathode pair 182 may be compared to the ECG waveform detected by the reference anode/cathode pair 184. In one embodiment, the P wave portion of the ECG trace detected by the proximal anode/cathode pair 180 and/or distal anode/cathode pair 182 is compared to P wave portion of the ECG trace detected by the reference anode/cathode pair 184 to determine whether the tip 112 of the CVC 100 is located within the SVC, right atrium, or right ventricle.

The deflection of the trace, i.e., its vertical height relative to the baseline may be used to compare the P waves of the proximal and distal anode/cathode pairs 180 and 182. The deflection of the trace may also be used to compare the P waves of the proximal anode/cathode pair 180 and/or distal anode/cathode pair 182 to the reference anode/cathode pair 184. Because a P wave constitutes a voltage change over time, the deflection of the P wave is not constant. In one embodiment, the P wave is represented by an array or series of discrete numerical values.

The deflection value may be calculated in several ways. For example, the maximum or peak deflection may be used. Alternatively, the deflection value may be calculated as the difference between the maximum deflection and the minimum deflection. The deflection value may also be calculated as the sum of the absolute value of the maximum and minimum deflections. If the P wave has two peaks, which may occur when one of the anode/cathode pairs 180 and 182 are located within the right atrium (see position 4 of FIGS. 2A and 2B), the deflection value may be calculated by totaling the absolute value of the two peaks. When this method is used, the deflection value of the P wave measured at positions 3-5 may all be approximately be equal. Further, if discrete data is being used, the discrete deflection quantities may be totaled. If continuous data is being used, the integral under the P wave may be used. Further, the average P wave deflection may be used. Because the polarity of portions of the P wave change depending upon the location of the anode/cathode pairs 180 and 182, it may be beneficial to use the absolute value of the deflection of the P wave to calculate the deflection value.

For the purposes of this application, the term "deflection value" will be used hereafter to describe the metric used to compare the P waves detected by the proximal and distal anode/cathode pairs 180 and 182. The deflection value may also be used to compare the P wave detected by the reference anode/cathode pair 184 to the P wave detected by one or both of the proximal and distal anode/cathode pairs 180 and 182. It is appreciated by those of ordinary skill in the art that the deflection value may be determined in numerous ways including those listed above and others not listed and the invention is not limited by the method and manner of determining the deflection value of the P wave.

In one exemplary embodiment, the deflection value is calculated as the sum of the absolute value of the maximum and minimum deflections when the maximum and minimum deflections have opposite polarities. The deflection value is calculated as the larger of the absolute value of the maximum and minimum deflections when the maximum and minimum deflections have the same polarity. In other words, the vertical height of the P wave is used. A first ratio of the deflection value of the distal anode/cathode pair 182 to the deflection value of the proximal anode/cathode pair 180 may be calculated.

When both of the anode/cathode pairs 180 and 182 are within the SVC, the deflection value of the P wave detected by each of them is substantially identical and the first ratio of their P wave deflection values equals approximately one. The deflection value of one or both of the P waves may be stored or otherwise recorded.

The user or operator may wish to continue advancing the CVC until the sino-atrial node is detected. When an anode/cathode pair 180 or 182 is approximately 1 cm to approximately 2 cm proximal to the sino-atrial node and therefore, by inference, approximately 1 cm to approximately 2 cm proximal to the entrance of the right atrium, the deflection value of the P wave detected by that anode/cathode pair may increase.

When the distal anode/cathode pair 182 enters the right atrium and the proximal anode/cathode pair 180 is still in the SVC, the deflection value of the P wave detected by the distal anode/cathode pair 182 may be at least double the deflection value of the P wave detected by the proximal anode/cathode pair 180. Therefore, the first ratio of the P wave deflection values of the distal anode/cathode pair 182 to the proximal anode/cathode pair 180 is greater than or equal to two. When this happens, the user or operator should withdraw the CVC 100.

A predetermined maximum threshold value may be used to determine whether the user or operator should withdraw the CVC 100. If the first ratio exceeds the maximum threshold value, the CVC 100 should be withdrawn. In one embodiment, the maximum threshold value may be approximately two.

When the distal anode/cathode pair 182 enters the right ventricle, the proximal anode/cathode pair 180 may be in the right atrium. Because the deflection value of the P wave experienced in the right ventricle is approximately equal to the deflection value of the P wave experienced in the SVC, the first ratio of the P wave deflection values of the distal anode/cathode pair 182 to the proximal anode/cathode pair 180 is less than or equal to about one half. Therefore, when the ratio is less than about one half, the user or operator should withdraw the CVC 100.

A predetermined minimum threshold value may be used to determine whether the user or operator should withdraw the CVC 100. If the first ratio is less than the minimum threshold value, the CVC 100 should be withdrawn. In one embodiment, the minimum threshold value may be approximately one half.

The distal anode/cathode pair 182 and the proximal anode/cathode pair 180 may be in the right atrium at the same time. When this occurs, the deflection value of the P waves detected by each would be very similar if not identical making their first ratio approximately equal to one. Therefore, a second ratio may be calculated to determine the location of the tip 112 of the CVC 100. The second ratio may include the ratio of the deflection value of the P wave detected by the proximal anode/cathode pair 180 to the deflection value of the P wave detected in the SVC. In one embodiment, the second ratio may include the ratio of the deflection value of the P wave detected by the proximal anode/cathode pair 180 to the deflection value of the P wave detected by the reference anode/cathode pair 184. In embodiments that include a reference anode/cathode pair 184, the reference anode/cathode pair 184 may detect the P wave in the SVC. Because the proximal anode/cathode pair 180 is inside the right atrium the deflection value of its P wave is greater than or equal to twice the deflection value of the P wave observed in the SVC. When the second ratio is equal to or greater than two, the user or operator should withdraw the CVC 100. The predetermined maximum threshold value may be used to determine whether the user or operator should withdraw the CVC 100. If the second ratio exceeds the maximum threshold value, the CVC 100 should be withdrawn.

Alternatively, a third ratio may be calculated to determine the location of the tip 112 of the CVC 100. The third ratio may include the ratio of the deflection value of the P wave detected by the distal anode/cathode pair 182 to the deflection value of the P wave detected in the SVC. In one embodiment, the third ratio may include the ratio of the deflection value of the P wave detected by the distal anode/cathode pair 182 to the deflection value of the P wave detected by the reference anode/cathode pair 184. In embodiments that include a reference pair 184, the reference pair 184 may detect the P wave in the SVC. Because the distal anode/cathode pair 182 is inside the right atrium, the deflection value of its P wave is greater than or equal to twice the deflection value of the P wave observed in the SVC. When third ratio is equal to or greater than two, the user or operator should withdraw the CVC 100. Under these circumstances, the predetermined maximum threshold value may be used to determine whether the user or operator should withdraw the CVC 100, i.e., if the third ratio exceeds the maximum threshold value, the CVC 100 should be withdrawn.

Determining when to withdraw the CVC 100 is unaffected by wide anatomic variability between individual people because instead of using predetermined threshold deflection values, the first, second, and/or third ratio of the deflection values obtained from each individual is used.

The following table summarizes the relationship between the location of the tip 112 of the CVC 100 and the deflection values of the P waves detected by the proximal and distal anode/cathode pairs 180 and 182:

| | Location of the distal anode/cathode pair 182 | | | |
|---|---|---|---|---|
| | SVC | Right Atrium | Right Atrium | Right Ventricle |
| | Location of the proximal anode/cathode pair 180 | | | |
| | SVC | SVC | Right Atrium | Right Atrium |
| First Ratio: Ratio of the deflection value of the distal anode/cathode pair 182 to the deflection value of the proximal anode/cathode pair 180 | ≈1 | ≧2 | ≈1 | ≦0.5 |
| Second Ratio: Ratio of the deflection value of the P wave detected by the proximal anode/cathode pair 180 and the deflection value of the P wave detected in the SVC | ≈1 | ≈1 | ≧2 | ≧2 |

-continued

| | Location of the distal anode/cathode pair 182 | | | |
|---|---|---|---|---|
| | SVC | Right Atrium | Right Atrium | Right Ventricle |
| | Location of the proximal anode/cathode pair 180 | | | |
| | SVC | SVC | Right Atrium | Right Atrium |
| Third Ratio: Ratio of the deflection value of the P wave detected by the distal anode/cathode pair 182 and the deflection value of the P wave detected in the SVC | ≈1 | ≧2 | ≧2 | ≈1 |

Because the voltage across each of the anode/cathode pairs 180 and 182 may vary depending over time, the voltage across wires 164 and 166 and wires 160 and 162 may each constitute a time-varying signal that can be analyzed using standard signal processing methods well known in the art. In a typical patient, the maximum of voltage across the anode/cathode pairs 180 and 182 may range from about 0.2 mV to about 3 mV. The signal from each anode/cathode pairs 180 and 182 may be amplified and/or filtered to improve the signal quality. A distal signal may be detected by the distal anode/cathode pair 182 and a proximal signal may be detected by the proximal anode/cathode pair 180. Similarly, an optional reference signal may be detected by the reference anode/cathode pair 184.

A separate ECG trace may be constructed for distal and proximal signals. In some embodiments, an ECG trace may also be constructed for the reference signal. The P wave portion of one or more of these ECG traces may be identified and analyzed. For example, the ECG trace of the distal signal may be visualized by connecting wires 164 and 166 of the distal anode/cathode pair 182 to a device such as a PACERVIEW® signal conditioner designed specifically to construct and display an ECG trace from a time varying low voltage signal. Similarly, the ECG trace of the proximal signal may be viewed by connecting the wires 160 and 162 of the proximal anode/cathode pair 180 to a PACERVIEW® signal conditioner. The ECG trace of the reference signal may be viewed by connecting the wires 167 and 168 of the proximal anode/cathode pair 184 to a PACERVIEW® signal conditioner.

In one embodiment, each of the four wires 160, 162, 164, and 166 may be coupled to a signal analysis system for analysis of the voltage information detected by the electrodes 150, 152, 154, and 156, respectively. In embodiments including electrodes 157 and 158, the wires 167 and 168 may be coupled to the signal analysis system for analysis of the voltage information detected by the electrodes 157 and 158, respectively. An exemplary signal analysis system 200 for analyzing the signals carried by wires 160, 162, 164, and 166 and alerting the user or operator when to withdraw the tip 112 of the CVC 100 may be viewed in FIG. 4. In an alternate embodiment, the system 200 may also analyze the signals carried by wires 167 and 168.

FIG. 5 is a block diagram of the components of the exemplary system 200. The system 200 may include a programmable central processing unit (CPU) 210 which may be implemented by any known technology, such as a microprocessor, microcontroller, application-specific integrated circuit (ASIC), digital signal processor (DSP), or the like. The CPU 200 may be integrated into an electrical circuit, such as a conventional circuit board, that supplies power to the CPU 210. The CPU 210 may include internal memory or memory 220 may be coupled thereto. The memory 220 may be coupled to the CPU 210 by an internal bus 264.

The memory 220 may comprise random access memory (RAM) and read-only memory (ROM). The memory 220 contains instructions and data that control the operation of the CPU 210. The memory 220 may also include a basic input/output system (BIOS), which contains the basic routines that help transfer information between elements within the system 200. The present invention is not limited by the specific hardware component(s) used to implement the CPU 210 or memory 220 components of the system 200.

Optionally, the memory 220 may include external or removable memory devices such as floppy disk drives and optical storage devices (e.g., CD-ROM, R/W CD-ROM, DVD, and the like). The system 200 may also include one or more I/O interfaces (not shown) such as a serial interface (e.g., RS-232, RS-432, and the like), an IEEE-488 interface, a universal serial bus (USB) interface, a parallel interface, and the like, for the communication with removable memory devices such as flash memory drives, external floppy disk drives, and the like.

The system 200 may also include a user interface 240 such as a standard computer monitor, LCD, colored lights 242 (see FIG. 4), PACERVIEW® signal conditioner, ECG trace display device 244 (see FIG. 4), or other visual display including a bedside display. In one embodiment, a monitor or handheld LCD display may provide an image of a heart and a visual representation of the estimated location of the tip 112 of the CVC 100. The user interface 240 may also include an audio system capable of playing an audible signal. In one embodiment, the user interface 240 includes a red light indicating the CVC 100 should be withdrawn and a green light indicating the CVC 100 may be advanced. In another embodiment, the user interface 240 includes an ECG trace display device 244 capable of displaying the ECG trace of the distal and proximal signals. In the embodiment depicted in FIG. 4, the user interface 240 includes a pair of lights 242, one red and the other green, connected in series with a ECG trace display device 244. In some embodiments, a display driver may provide an interface between the CPU 210 and the user interface 240.

The user interface 240 may permit the user to enter control commands into the system 200. For example, the user may command the system 200 to store information such as the deflection value of the P wave inside the SVC. The user may also use the user interface 240 to identify which portion of the ECG trace corresponds to the P wave. The user interface 240 may also allow the user or operator to enter patient information and/or annotate the data displayed by user interface 240 and/or stored in memory 220 by the CPU 210. The user interface 240 may include a standard keyboard, mouse, track ball, buttons, touch sensitive screen, wireless user input device and the like. The user interface 240 may be coupled to the CPU 210 by an internal bus 268.

Optionally, the system 200 may also include an antenna or other signal receiving device (not shown) such as an optical sensor for receiving a command signal such as a radio frequency (RF) or optical signal from a wireless user interface device such as a remote control. The system 200 may also include software components for interpreting the command signal and executing control commands included in the command signal. These software components may be stored in memory 220.

The system 200 includes an input signal interface 250 for receiving the distal and proximal signals. The input signal interface 250 may also be configured to receive the reference signal. The input signal interface 250 may include any standard electrical interface known in the art for connecting a double dipole lead wire to a conventional circuit board as well as any components capable of communicating a low voltage time varying signal from a pair of wires through an internal bus 262 to the CPU 210. The input signal interface 250 may include hardware components such as memory as well as standard signal processing components such as an analog to digital converter, amplifiers, filters, and the like.

The various components of the system 200 may be coupled together by the internal buses 262, 264, and 268. Each of the internal buses 262, 264, and 268 may be constructed using a data bus, control bus, power bus, I/O bus, and the like.

The system 200 may include instructions 300 executable by the CPU 210 for processing and/or analyzing the distal and/or proximal signals. These instructions may include computer readable software components or modules stored in the memory 220. The instructions 300 may include an ECG Trace Generator Module 310 that generates a traditional ECG trace from the distal and/or proximal signals. In some embodiments, the ECG Trace Generator Module 310 may generate a traditional ECG trace from the reference signal. As is appreciated by those of ordinary skill in the art, generating an ECG trace from an analog signal, such as the distal and proximal signals, may require digital or analog hardware components, such as an analog to digital converter, amplifiers, filters, and the like and such embodiments are within the scope of the present invention. In one embodiment, some or all of these components may be included in the input signal interface 250. In an alternate embodiment, some or all of these components may be implemented by software instructions included in the ECG Trace Generator Module 310. The ECG Trace Generator 310 may include any method known in the art for generating an ECG trace from a time varying voltage signal.

The instructions 300 may include a P Wave Detection Module 320 for detecting or identifying the P wave portion of the ECG trace. The P wave portion of the ECG trace may be detected using any method known in the art. In one embodiment, the P Wave Detection Module 320 receives input from the user or operator via the user interface 240. The input received may identify the P wave portion of the ECG trace.

The instructions 300 may include an Interpretive Module 330 for comparing the P wave generated for the distal, proximal, and/or reference signals. In one embodiment, the Interpretive Module 330 determines the deflection value of the P wave generated for the distal and/or proximal signals. In some embodiments, the Interpretive Module 330 determines the deflection value of the P wave generated for the reference signal. The Interpretive Module 330 may direct the CPU 210 to store the deflection value of the distal, proximal, and/or reference signals in memory 220. In particular, it may be desirable to store the deflection value of the P wave encountered in the SVC. The Interpretive Module 330 may receive input from the user or operator via the user interface 240 instructing the Interpretive Module 330 to store the deflection value.

The Interpretive Module 330 may also determine the first ratio by calculating the ratio of the deflection value of the distal signal to the deflection value of the proximal signal. If the first ratio is approximately equal to or greater than the maximum threshold value, the tip 112 of the CVC 100 may be in the right atrium. The Interpretive Module 330 may alert the user or operator that the tip 112 is in the right atrium and the CVC 100 should be withdrawn from the right atrium. On the other hand, if the first ratio is approximately equal to or less than the minimum threshold value, the tip 112 of the CVC 100 may be in the right ventricle. The Interpretive Module 330 may alert the user or operator that the tip 112 is in the right ventricle and the CVC 100 should be withdrawn therefrom.

If the first ratio is less than the maximum threshold value and greater than the minimum threshold value, the tip 112 may be in either the right atrium or the SVC. When this happens, the Interpretive Module 330 may calculate either the second ratio or third ratio. If the second or third ratio is approximately equal to or greater than the maximum threshold value, the tip may be in the right atrium and should be withdrawn therefrom. The Interpretive Module 330 may alert the user or operator that the tip 112 is in the right atrium. If the second or third ratio is approximately less than the maximum threshold value, the tip 112 is in the SVC and may be advanced if the operator so chooses. The Interpretive Module 330 may communicate to the user or operator that the tip 112 may be advanced.

In an alternate embodiment, the second ratio may be calculated first. Whenever the second ratio is approximately equal to or greater than the maximum threshold value, the user or operator may be alerted to withdraw the CVC 100. If the second ratio is approximately less than the maximum threshold value, the first or third ratio may be calculated and used to determine the position of the tip 112 of the CVC 100.

In one embodiment, the instructions in the Interpretive Module 330 direct the CPU 210 to use the user interface 240 to communicate whether the tip 112 should be withdrawn to the user. The CPU 210 may use the user interface 240 to communicate the tip 112 may be advanced.

While exemplary minimum and maximum threshold values have been provided as a general guideline, those of ordinary skill in the art appreciate that these values may benefit from adjustment as additional anatomic or electrophysiologic data is acquired and such modified values are within the scope of the present invention. Because the Interpretive Module 330 may interpret the P wave to obtain the deflection values of the distal and proximal signals, compare the deflection values and provide the operator with immediate real-time feedback, the operator need not interpret the actual ECG waveforms.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of locating a tip of a central venous catheter having a portion disposed within the superior vena cava, the catheter comprising a distal pair of electrodes and a proximal pair of electrodes spaced longitudinally from the distal pair of electrodes, the method comprising:
   obtaining a distal electrical signal from the distal pair of electrodes;
   generating a first P wave from the distal signal;
   obtaining a proximal electrical signal from the proximal pair of electrodes;
   generating a second P wave from the proximal signal;
   comparing the first and second P waves;
   obtaining a reference electrical signal in the superior vena cava;
   generating a reference P wave from the reference electrical signal;
   comparing the reference P wave with at least one of the first and second P waves; and
   determining a location of the tip of the central venous catheter based on the comparison of the first and second P waves and the comparison of the reference P wave with at least one of the first and second P waves.

2. The method according to claim 1, wherein the first P wave has a first shape, the second P wave has a second shape, and the reference P wave has a reference shape, comparing the first and second P waves comprising comparing the first and second shapes, and comparing the reference P wave with at least one of the first and second P waves comprising comparing the reference shape with at least one of the first and second shapes.

3. The method according to claim 2, wherein the first shape has a first height and the second shape has a second height, determining the location of the tip of the central venous catheter based on the comparison of the first and second P waves and the comparison of the reference P wave with at least one of the first and second P waves comprising concluding the tip of the central venous catheter is located in the right atrium when the first height is at least twice the second height.

4. The method according to claim 2, wherein the first shape has a first height and the second shape has a second height, determining the location of the tip of the central venous catheter based on the comparison of the first and second P waves and the comparison of the reference P wave with at least one of the first and second P waves comprising concluding the tip of the central venous catheter is located in the right ventricle when the first height is at most half the second height.

5. The method according to claim 2, wherein the first shape has a first height, the second shape has a second height, and the reference shape has a reference height, determining the location of the tip of the central venous catheter based on the comparison of the first and second P waves and the comparison of the reference P wave with at least one of the first and second P waves comprising:
   concluding the tip of the central venous catheter is located in the superior vena cava when the first height is approximately equal to both the second height and the reference height; and
   concluding the tip of the central venous catheter is located in the right atrium when the first height is approximately equal to the second height and greater than the reference height.

6. The method according to claim 2, wherein determining the location of the tip of the central venous catheter based on the comparison of the first and second P waves and the comparison of the reference P wave with at least one of the first and second P waves comprises concluding the tip of the central venous catheter is located in the right ventricle when the first shape approximates a mirror image of the reference shape about a horizontal axis.

7. The method according to claim 2, wherein the first shape has a first height and the reference shape has a reference height, determining the location of the tip of the central venous catheter based on the comparison of the first and second P waves and the comparison of the reference P wave with at least one of the first and second P waves comprising concluding the tip of the central venous catheter is located in the right atrium when the first height is at least twice the reference height.

8. The method according to claim 2, wherein the first shape has a first height, the second shape has a second height, and the reference shape has a reference height, determining the location of the tip of the central venous catheter based on the comparison of the first and second P waves and the comparison of the reference P wave with at least one of the first and second P waves comprising:

concluding the tip of the central venous catheter is located in the superior vena cava when the first height is approximately equal to both the second height and the reference height; and concluding the tip of the central venous catheter is located in the right ventricle when the first height is approximately equal to the reference height and is less than the second height.

9. The method according to claim 2, wherein the second shape has a second height and the reference shape has a reference height, determining the location of the tip of the central venous catheter based on the comparison of the first and second P waves and the comparison of the reference P wave with at least one of the first and second P waves comprising concluding the tip of the central venous catheter is located in the right atrium or right ventricle when the second height is at least twice the reference height.

10. The method according to claim 2, wherein the first shape has a first height, the second shape has a second height, and the reference shape has a reference height, determining the location of the tip of the central venous catheter based on the comparison of the first and second P waves and the comparison of the reference P wave with at least one of the first and second P waves comprising:

concluding the tip of the central venous catheter is located in the superior vena cava when the second height is approximately equal to both the first height and the reference height; and concluding the tip of the central venous catheter is located in the right atrium when the second height is approximately equal to the reference height and is less than the first height.

11. The method according to claim 1, wherein the portion of the central venous catheter disposed within the superior vena cava includes a reference pair of electrodes, obtaining the reference electrical signal in the superior vena cava comprising obtaining the reference electrical signal from the reference pair of electrodes.

* * * * *